(12) United States Patent
Tonge et al.

(10) Patent No.: US 10,071,965 B2
(45) Date of Patent: Sep. 11, 2018

(54) PYRIDONE FABI INHIBITORS AND USES THEREOF

(71) Applicant: The Research Foundation for The State University of New York, Albany, NY (US)

(72) Inventors: Peter Tonge, Setauket, NY (US); Pan Pan, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/130,365

(22) Filed: Apr. 15, 2016

(65) Prior Publication Data

US 2016/0376235 A1    Dec. 29, 2016

Related U.S. Application Data

(60) Provisional application No. 62/148,058, filed on Apr. 15, 2015.

(51) Int. Cl.
  *C07D 213/69*    (2006.01)
  *C07D 213/64*    (2006.01)

(52) U.S. Cl.
  CPC ......... *C07D 213/69* (2013.01); *C07D 213/64* (2013.01)

(58) Field of Classification Search
  CPC .................................................. C07D 213/69
  USPC ............................................... 546/296
  See application file for complete search history.

(56) References Cited

PUBLICATIONS

Li et al., "A Structural and Energetic, etc.," ACS Chem. Biol. 2014,9,986-993.*
Schiebel et al., "Rational Design, etc.," Journal of Biological Chemistry, 289(23), 15987-16005 and S-1 to S-19.*

* cited by examiner

*Primary Examiner* — Patricia L Morris
(74) *Attorney, Agent, or Firm* — Hoffmann & Baron, LLP

(57) ABSTRACT

The present invention provides novel 2-pyridone compounds and 4-pyridone compounds and methods of treating a subject infected with a pathogen of *Staphylococcus aureus, Mycobacterium tuberculosis, Francisella tularensis, Burkholderia pseudomallei, Yersinia pestis, Escherichia coli* and *Proteus mirabilisone.*

1 Claim, 16 Drawing Sheets
Specification includes a Sequence Listing.

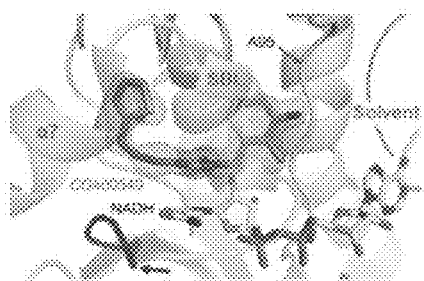
Figure 6A
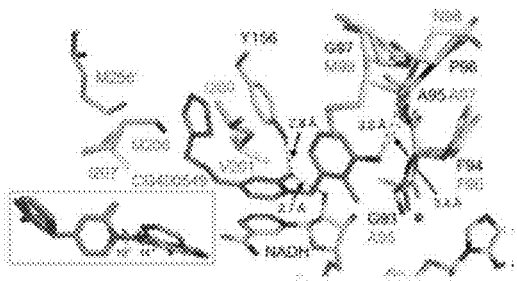
Figure 6B
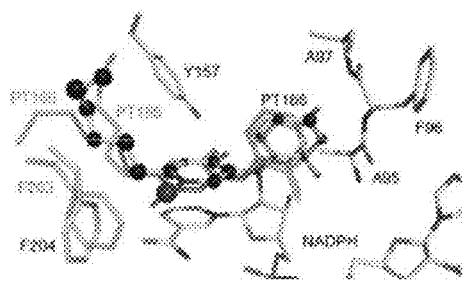
Figure 6C
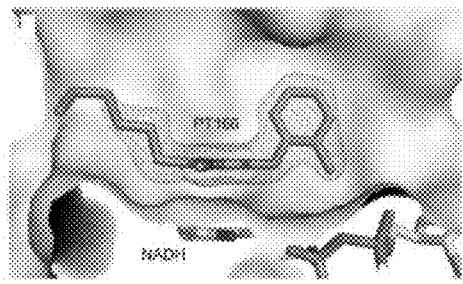
Figure 6D

Figure 7

PYRIDONE FABI INHIBITORS AND USES THEREOF

CROSS-REFERENCE TO RELATED APPLICATION

This application claims the benefit of U.S. Provisional Application Ser. No. 62/148,058, filed Apr. 15, 2015, which is incorporated herein by reference in its entirety.

This invention was made with government support under grant numbers AI070383 and AI044639 awarded by the National Institute of Health. The government has certain rights in the invention.

BACKGROUND OF THE INVENTION

*Staphylococcus aureus* can cause a variety of bacterial infections ranging from common skin infections to life-threatening pneumonia or bacteremia (Pantosti et al. (2009) What is MRSA? Eur. Respir. J. 34:1190-1196). In particular, methicillin-resistant *S. aureus* (MRSA) poses an imminent risk to immunocompromised patients in healthcare settings all over the world. In addition, the incidence of community-acquired MRSA infections has increased among otherwise healthy individuals (Naimi et al. (2003) Comparison of community- and health care-associated methicillin-resistant *Staphylococcus aureus* infection. JAMA 290:2976-2984). The initial occurrence of *S. aureus* strains resistant to vancomycin, an antibiotic used to treat severe MRSA infections, underlines the urgent need for novel anti-staphylococcal drugs (Sievert et al. (2008) Vancomycin-resistant *Staphylococcus aureus* in the United States, 2002-2006. Clin. Infect. Dis. 46:668-674).

BRIEF DESCRIPTION OF FIGURES

FIG. 6A is a depiction of rationalizing the *Staphylococcus*-specific activity of CG400549 and designing PT166 with an extended activity spectrum. CG400549 in its complex with ecFabI and NADH. The $2F_o$-$F_c$ omit map is depicted for CG400549 (shown as mesh at 1σ) and clearly reveals the presence of this molecule, although the SBL region was found to be disordered in this structure (the disordered region starts after residue 192 as highlighted by an arrow. As a reference, the SBL of a superimposed ecFabI-NAD$^+$-triclosan structure is shown (PDB code 1QSG) (13). Together with the SBL, the loop comprising Ala-95 defines a portal toward the solvent.

FIG. 6B. Comparison between the CG400549-bound *S. aureus* (for clarity only present in the inset) and ecFabI ternary complexes. The inset contains a comparison between the CG400549 binding modes, which differ in their B-ring conformations via changes in the torsion angles between the two aromatic rings (indicated by arrowheads). Met-256' of the subunit is on the opposite side of the ecFabI homotetramer. Residues Ile-200 and Met-206 of the 1QSG structure (ecFabI-NAD$^+$-triclosan) are shown as reference.

FIG. 6C. Putative binding mode of PT166 within the saFabI pocket (CG400549-I structure, subunit A). PT166 was docked into the saFabI binding cavity using the validated approach described under "Experimental Procedures." The radii of the spheres indicate the values of the favorable (unfavorable) score for each individual atom, as determined with DrugScoreX. The bpFabI-NAD$^+$-PT155 structure confirms this binding mode and suggests a rotation of Phe-204 to avoid the steric interference with the N-methyl group of 4-pyridone inhibitors (indicated by the sphere). Moreover, the putative binding mode is in accordance with the PT166-bound ecFabI structure (subunit A). The docking results for the residual pyridone inhibitors of Table 1 are summarized in supplemental FIG. S1 of Schiebel et al., *The Journal of Biological Chemistry*, 2014, 289(23):15987-16005.

FIG. 6D. $2F_o$-$F_c$ omit map (shown as mesh at 1σ) for PT166 bound to ecFabI. An intersection of the ecFabI-NADH-PT166 structure (subunit A) is shown. The SBL, which usually covers the binding site (in front of the cavity) is disordered.

FIG. 7 is an alignment of FabI sequences from clinically relevant pathogens. The sequences of FabI from *S. aureus* (saFabI), *S. epidermidis* (seFabI), *E. coli* (ecFabI), *B. pseudomallei* (bpFabI), *F. tularensis* (ftFabI), *H. influenzae* (hiFabI), *Neisseria gonorrhoeae* (ngFabI), *Neisseria meningitidis* (nmFabI), *Moraxella catarrhalis* (mcFabI), *Proteus mirabilis* (pmFabI), *H. pylori* (hpFabI) and *M. tuberculosis* (InhA) were aligned using ClustalW (Larkin et al. (2007) Clustal W and Clustal X, Version 2.0. Bioinformatics 23: 2947-8). These organisms are known to contain FabI as the sole enoyl-ACP reductase (exception: FabV is additionally present in *B. pseudomallei*) (Lu et al. (2010) Mechanism and inhibition of the FabV enoyl-ACP reductase from *Burkholderia mallei*. Biochemistry 49:1281-9). Residues that are likely responsible for the unique NADPH specificity, enhanced mobility, and enlarged binding pocket of saFabI are indicated. The C-terminal regions occluding the acyl-binding cavity and the RKXXS motif conferring NADPH specificity are highlighted with boxes. The star indicates the location of Met-99. This figure was prepared using ESPript (Gouet et al. (1999) ESPript: analysis of multiple sequence alignments in PostScript. Bioinformatics 15:305-8).

SUMMARY OF THE INVENTION

Figure 1A:
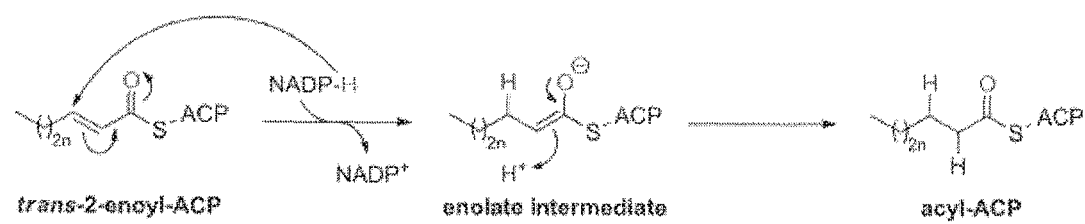
FIG. 1A is a depiction of the catalyzed reaction and successful inhibitor classes of *S. aureus* FabI. FabI catalyzes the reduction of the trans-2-enoyl-ACP substrate via an enolate intermediate (n=0-8) (White et al. (2005) The structural biology of type II fatty acid biosynthesis. Annu. Rev. Biochem. 74:791-831). In the case of saFabI, the hydride is delivered by the reducing agent NADPH. During the second step of the reaction, the enolate intermediate is protonated, which leads to the formation of the final acyl-ACP product.
Figure 1B:
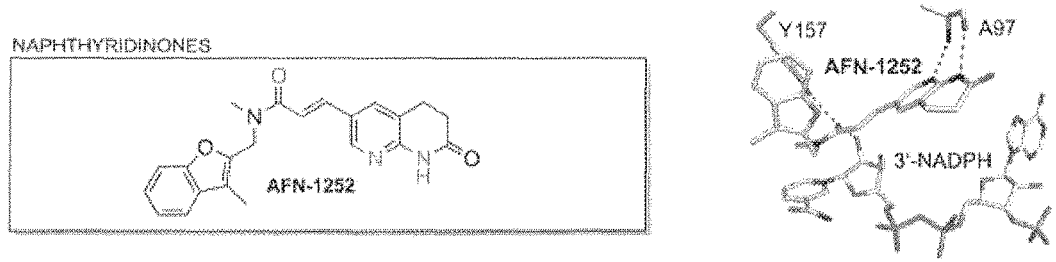
FIG. 1B FabI inhibitor class AFN-1252 along with its binding mode in the saFabI active site pocket (PDB codes 4FS3 and 4ALI; the CG400549 structure was solved during this study, PDB code 4CV1). AFN-1252 is currently in clinical trials (Gerusz, V. (2010) in Annual Reports in Medicinal Chemistry (John, E. M., ed) pp. 295-311, Academic Press, New York). One common feature of these FabI inhibitors is the formation of a hydrogen bond to Tyr-157 and the cofactor NADP(H). In addition, all depicted inhibitors directly interact with Ala-97.
Figure 1C:
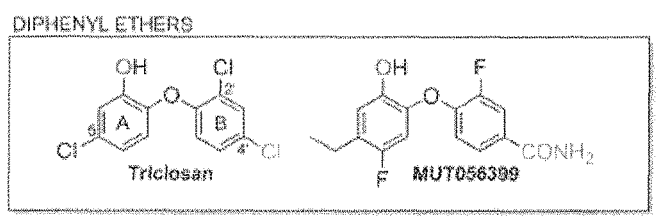
FIG. 1C. A Fab1 inhibitor class MUT056399.
Figure 1C:
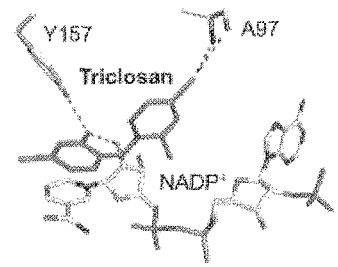
Figure 1D:
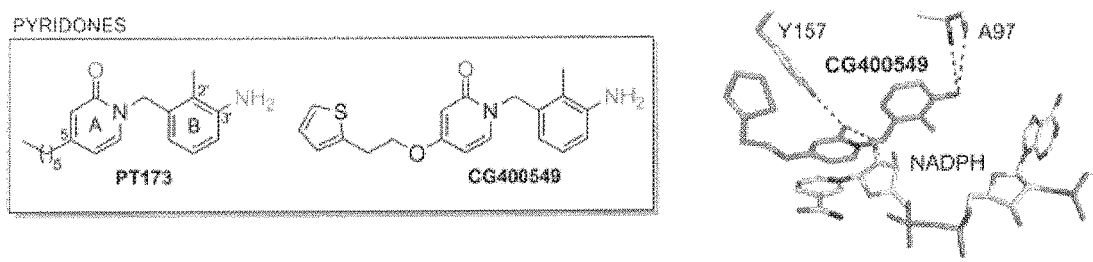
FIG. 1D. A Fab1 inhibitor class CG400549.

In one embodiment, the present invention provides 2-pyridone compounds having the formula:

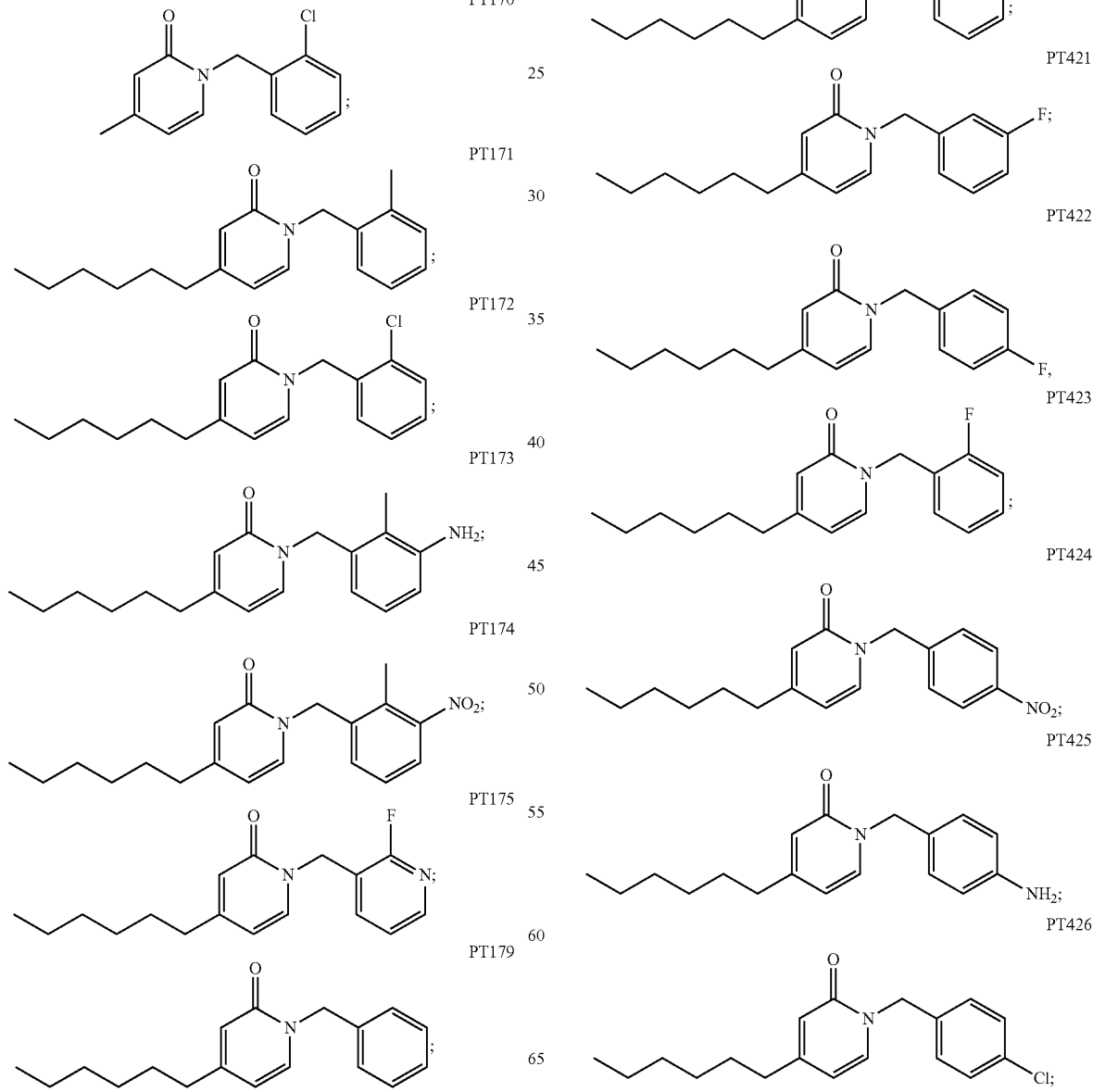

PT427

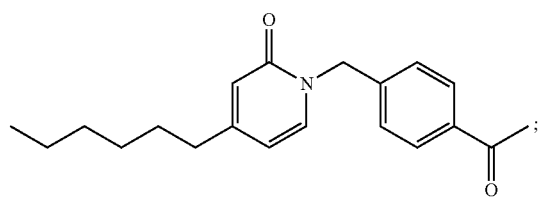

or a pharmaceutically acceptable salt thereof.

In another embodiment, the present invention provides methods of treating a subject infected with a pathogen selected from the group consisting of *Staphylococcus aureus, Mycobacterium tuberculosis, Francisella tularensis, Burkholderia pseudomallei, Yersinia pestis, Escherichia coli* and *Proteus mirabilis*. The method comprises administering to the subject the aforementioned 2-pyridone compounds or pharmaceutically acceptable salts thereof.

In another embodiment, the present invention provides 4-pyridone compounds having the formula:

PT151

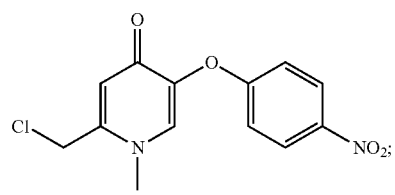

PT152

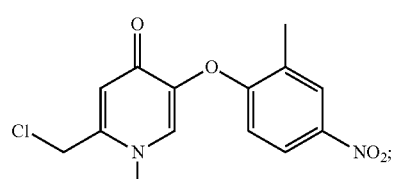

PT155

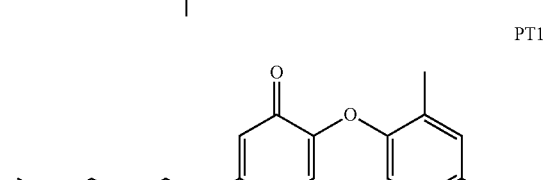

PT156

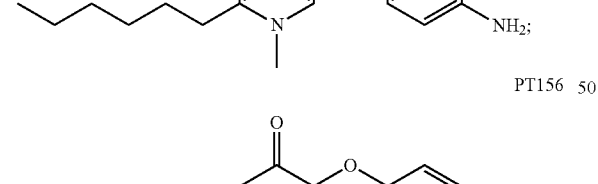

PT157

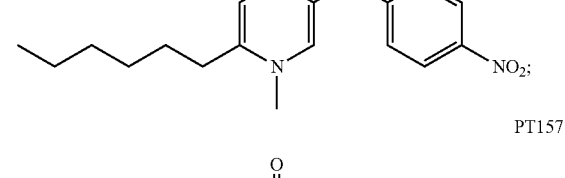

PT159

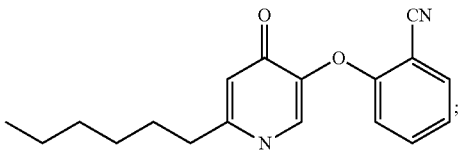

PT165

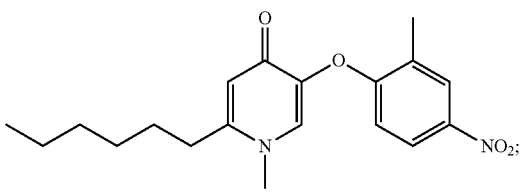

PT166

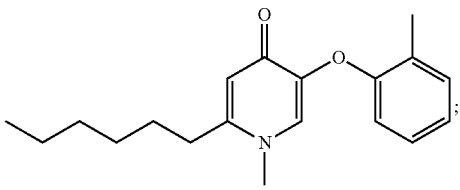

PT167

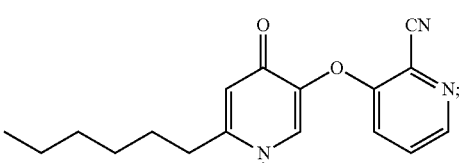

PT168

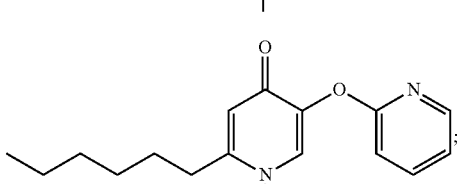

PT169

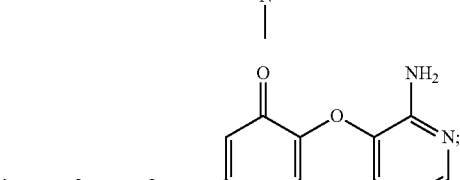

PT190

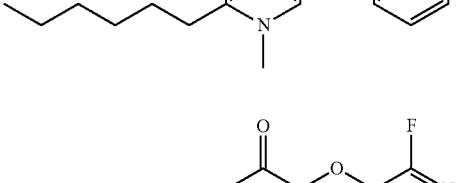

or a pharmaceutically acceptable salt thereof.

In one embodiment, the present invention provides methods of treating a subject infected with a pathogen selected from the group consisting of *Staphylococcus aureus, Mycobacterium tuberculosis, Francisella tularensis, Burkholderia pseudomallei, Yersinia pestis, Escherichia coli* and *Proteus mirabilis*. The method comprises administering to the subject an aforementioned 4-pyridone compound or a pharmaceutically acceptable salt thereof.

DETAILED DESCRIPTION OF THE INVENTION

The invention relates to 2-pyridone and 4-pyridone compounds. These compounds inhibit the enoyl-ACP reductase FabI enzyme in the bacterial fatty acid biosynthesis pathway. Some embodiments of these compounds are shown in Tables 1A and 2A. These 2-pyridone and 4-pyridone compounds, or pharmaceutically acceptable salts thereof, can be used to treat an animal infected by a wide range of pathogens, including, for example, *Staphylococcus aureus, Mycobacterium tuberculosis, Francisella tularensis, Burkholderia pseudomallei, Yersinia pestis, Escherichia coli* and *Proteus mirabilis*.

For example, one of the 4-pyridone compounds, PT166, has an MIC of 0.24 μg/ml against *Staphylococcus aureus* strain RN4220 and inhibits the FabI enzyme in this organism with a $K_i$ value of 2.7 nM. In addition, PT166 demonstrates in vivo antibacterial efficacy against methicillin-resistant *S. aureus* (MRSA, strain BAA1762) in a neutropenic mouse thigh infection model. A 100 mg/kg intramuscular dose of PT166 significantly decreased the bacterial burden in the infected thigh by 2.8 log cfu/g tissue.

TABLE 1A

2-Pyridones

PT170, PT171, PT172, PT173, PT174, PT175

TABLE 1A-continued

2-Pyridones

PT179, PT191, PT192, PT420, PT421, PT422, PT423, PT424, PT425, PT426

TABLE 1A-continued

2-Pyridones

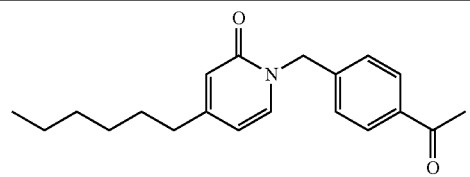
PT427

TABLE 2A

4-Pyridones

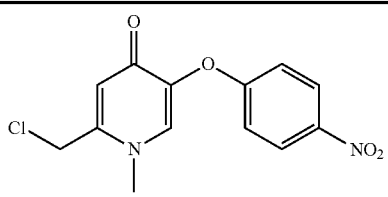
PT151

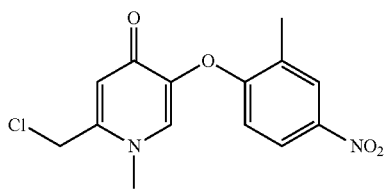 [SMILES: Cc1cc([N+](=O)[O-])ccc1Oc1cn(C)c(CCl)cc1=O]
PT152

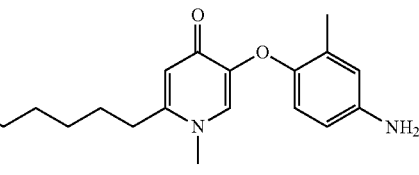
PT155

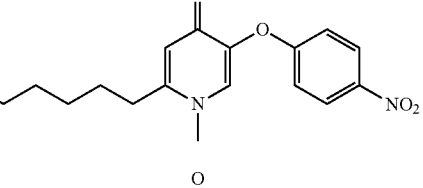
PT156

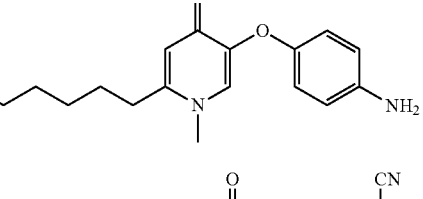
PT157

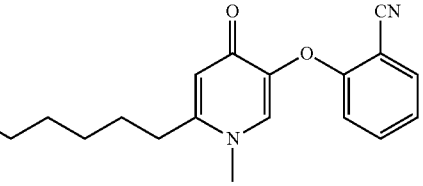
PT159

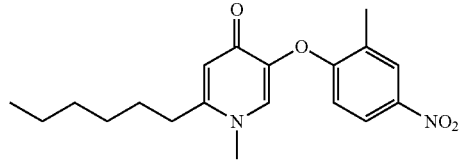 [SMILES: CCCCCCc1cc(=O)c(Oc2ccc([N+](=O)[O-])cc2C)cn1C]
PT165

TABLE 2A-continued

4-Pyridones

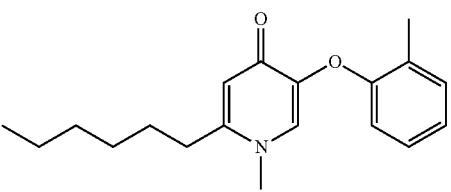 [SMILES: CCCCCCc1cc(=O)c(Oc2ccccc2C)cn1C]
PT166

PT167

PT168

PT169

PT190

Pharmaceutically Acceptable Salts

The present invention also relates to pharmaceutically acceptable salts of the 2-pyridone and 4-pyridone compounds. The pharmaceutically acceptable salts include the conventional non-toxic salts of the compounds as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the 2-pyridone and 4-pyridone compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Uses of the Pyridone Compounds

The invention also relates to methods of treating subjects infected with a wide range of pathogens including, for example, *Staphylococcus aureus, Mycobacterium tuberculosis, Francisella tularensis, Burkholderia pseudomallei, Yersinia pestis, Escherichia coli* and *Proteus mirabilis*. The method comprises administering to a subject a compound disclosed in Table 1A or Table 2A, or a pharmaceutically acceptable salt thereof. Included in subjects are humans and animals. Animals include mammals (such as, e.g., dogs, cats, ferrets, rabbits, guinea pigs, horses, cows), fish and birds.

In particular, the following compounds, and their pharmaceutically acceptable salts, have activity against *S. aureus, M. tuberculosis, F. tularensis, B. pseudomallei, Y. pestis, E. coli* and *P. mirabilis*: of the 2-pyridones, PT170, PT171, PT172, PT173, PT174, PT175, PT179, PT420, PT421, PT422, PT423, PT424, PT425, PT426, and PT427; and of the 4-pyridones, PT152, PT155, PT156, PT157, PT159, PT165, PT166, PT167, PT168, PT169 and PT190. The following 2-pyridone compounds, and their pharmaceutically acceptable salts, have activity against *M. tuberculosis, F. tularensis, B. pseudomallei, Y. pestis, E. coli* and *P. mirabilis*: PT191 and PT192. The following 4-pyridone compound, and its pharmaceutically acceptable salts, has activity against *S. aureus, F. tularensis, B. pseudomallei, Y. pestis, E. coli* and *P. mirabilis*: PT151.

The methods and compounds of the invention can be employed alone, or in combination with other anti-microbial agents. Other anti-microbial agents include, for example, isoniazid, rifampin, pyrazinamide, rifabutin, streptomycin and ciprofloxacin. The combination of these anti-microbial agents and the compounds of the invention provide agents for the treatment of infectious diseases.

An effective amount of a compound disclosed in Table 1A or Table 2A, or a pharmaceutically acceptable salt thereof, as used herein, is any amount effective to treat a subject infected with *S. aureus, M. tuberculosis, F. tularensis, B. pseudomallei, Y. pestis, E. coli* and *P. mirabilis*. Modes of administration and doses can be determined by those having skill in the art. An effective amount of the compound varies with the particular subject (species, age, gender, weight, etc.), the nature and severity of the condition to be treated, the particular compound administered, and its route of administration. Amounts suitable for administration to humans, and animals, are routinely determined by skilled artisans, e.g., physicians and clinicians.

For instance, for concentration-dependent antimicrobial compounds, the compounds are given at a dose whereby the plasma or tissue drug concentration exceeds the MIC of the compound by 10- to 12-fold. For time-dependent antimicrobial compounds, the compounds are given at a dose whereby the plasma or tissue drug concentration is above the MIC of the compound for most (e.g., 50-75%) of the dosing interval. A skilled artisan would know how to dose a compound to achieve such plasma/tissue drug concentration taking into account the particular subject to be treated, the location of the infected tissues/fluid, the particular antimicrobial, the particular microbe, the degree of infection, etc.

The minimum dose of a compound is the lowest dose at which efficacy is observed. For example, the minimum dose of a compound may be about 100 mg/day, about 200 mg/day, or about 400 mg/day.

The maximum dose of a compound is the highest dose at which efficacy is observed in a subject, and side effects are tolerable. For example, the maximum dose of a compound may be about 1200 mg/day, about 3000 mg/day, or about 6000 mg/day.

A pyridone compound useful in the methods of the present invention can be administered by any method known in the art. Some examples of suitable modes of administration include oral and systemic administration. Systemic administration can be enteral or parenteral. Liquid or solid (e.g., tablets, gelatin capsules) formulations can be employed.

Parenteral administration of the pyridone compound includes, for example, intraperitoneal, intravenous, intramuscular, and subcutaneous injections. For instance, a chemical compound can be administered to a subject by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a chemical compound can be accomplished by a nebulizer or liquid mist.

The chemical compound can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The chemical compound can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Typically, the stabilizer or combination of stabilizers constitutes from about 0.1% to about 10% weight for weight of the chemical compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v). Other preferred surfactants include Solutol H-15 and Cremophore EL.

The salt or buffering agent may be any salt or buffering agent, such as for example sodium chloride, or sodium/potassium phosphate, respectively. Typically, the buffering agent maintains the pH of the chemical compound formulation in the range of about 5.5 to about 7.5. The salt and/or buffering agent is also useful to maintain the osmolality at a level suitable for administration to a subject. Typically, the salt or buffering agent is present at a roughly isotonic concentration of about 150 mM to about 300 mM.

The chemical compound can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as, for example a morphine derivative; or an isotonic agent etc. As a further precaution against oxidation or other spoilage, the composition may be stored under nitrogen gas in vials sealed with impermeable stoppers.

EXAMPLES

Examples have been set forth below for the purposes of illustration and to describe the best mode of the invention at the present time. The scope of the invention is not to be in any way limited by the examples set forth herein.

Compound Synthesis

The pyridone compounds PT155, PT159, PT166, PT170, PT171, PT172, PT173, PT179, PT191, PT420, and CG400549 were synthesized as described in the supplemental Schemes S1-S5 found in Schiebel et al., *The Journal of Biological Chemistry*, Jun. 6, 2014, 289(23):15987-16005, the entirety of which is hereby incorporated by reference.

Expression and Purification saFabI was prepared as described previously (Schiebel et al. (2012) *Staphylococcus aureus* FabI: inhibition, substrate recognition, and potential implications for in vivo essentiality. Structure 20:802-13; Priyadarshi et al. (2010) Structural insights into *Staphylococcus aureus* enoyl-ACP reductase (FabI), in complex with NADP and triclosan. Proteins 78:480-6). Briefly, the safabi gene cloned into a pETM-11 vector in *E. coli* BL21(DE3) was expressed, the cells were disrupted, and obtained was the >95% pure protein in 25 mM Tris-HCl, pH 8.0, and 200 mM NaCl via $Ni^{2+}$ affinity and size exclusion chromatography. In addition, ecFabI and the *M. tuberculosis* enoyl-ACP reductase InhA were expressed and purified as described previously (Sivaraman et al. (2003) Structure-activity studies of the inhibition of FabI, the enoyl reductase from *Escherichia coli*, by triclosan: kinetic analysis of mutant FabIs. Biochemistry 42, 4406-13; Luckner et al. (2010) A slow, tight binding inhibitor of InhA, the enoyl-acyl carrier protein reductase from *Mycobacterium tuberculosis*. J. Biol. Chem. 285:14330-7). *Burkholderia pseudomallei* FabI (bpFabI) was obtained using a previously described procedure (Liu et al. (2011) Mechanism and inhibition of the FabI enoyl-ACP reductase from Burk-holderiapseudomallei. J. Antimicrob. Chemother. 66:564-73) with the final size exclusion chromatography step (Superdex 200 26/60, GE Healthcare/AKTA) performed in 20 mM BisTris-HCl, pH 6.5, 500 mM NaCl, 1 mM EDTA.

Crystallization

Prior to concentrating saFabI samples from 2 to 15-19 mg/ml, the protein was incubated for 2 h at 20° C. with a 12-fold molar excess of NADPH and a 20-fold molar excess of inhibitor dissolved in DMSO (CG400549 or PT173, respectively). Diffraction-quality crystals were grown in vapor diffusion experiments with a precipitant solution containing 0.1-0.2 M $Li_2SO_4$ and 20-24 w/v % PEG 3350. For CG400549, crystals were obtained of space group P212121 with two different sets of cell parameters (the resulting structures were named CG400549-I and CG400549-II; See Schiebel et al., *The Journal of Biological Chemistry*, Jun. 6, 2014, 289(23):15987-16005, supplemental Table S1).

Similarly, ecFabI samples at a concentration of 13 mg/ml were incubated for 2 h at 4° C. with a 10-fold molar excess of NADH and a 20-fold molar excess of CG400549 or PT166 (dissolved in DMSO), respectively. Hanging drop vapor diffusion experiments yielded diffraction-quality crystals in drops composed of 1 µl of this protein/ligand mixture and 1 µl of precipitant solution (0.2 $MNH_4Ac$, 0.1 M CAPS, pH 10.5, and 20 w/v % PEG 8000 in the case of CG400549; 0.2 M $NH_4Ac$, 0.1 M sodium citrate, pH 5.6, and 10 w/v % PEG 8000 in the case of PT166).

bpFabI samples at a concentration of 10-30 mg/ml were incubated for 2 h at 20° C. with a 10-fold molar excess of $NAD^+$ and a 20-fold molar excess of PT155 (dissolved in DMSO). Sitting drop vapor diffusion experiments yielded diffraction-quality crystals in drops composed of 0.3 µl of the protein/ligand mixture and 0.3 µl of precipitant solution (20 w/v % PEG 3350 and 200 mM $(NH_4)2HPO_4$).

Data Collection and Structure Determination

Prior to flash-freezing in liquid nitrogen, the saFabI ternary complex crystals were successively transferred into solutions composed of mother liquor supplemented with 10 and 25 v/v % ethylene glycol, respectively. Diffraction data were collected at the BESSY II MX beamline 14.1 (Mueller et al. (2012) Facilities for macromolecular crystallography at the Helmholtz-Zentrum Berlin. J. Synchrotron Radiat. 19:442-9) ($\lambda$=0.918 Å, T=100 K) equipped with a MarMosaic 225 detector, integrated with Imosflm (CG400549-II and PT173) (Leslie, A. G. (1992) Recent changes to the MOSFLM package for processing film and image plate data. Joint CCP4+ESF-EAMCB Newsletter on Protein Crystallography, No. 26) or XDS (CG400549-I) (Kabsch, W. (1993) Automatic processing of rotation diffraction data from crystals of initially unknown symmetry and cell constants. J. Appl. Crystallogr. 26:795-800), and further processed using Scala (Evans, P. (2006) Scaling and assessment of data quality. Acta Crystallogr. D Biol. Crystallogr. 62:72-82). The CG400549 structures were solved by molecular replacement with Phaser (McCoy et al. (2007) Phaser crystallographic software. J. Appl. Crystallogr. 40:658-74) using previously published saFabI structure (PDB code 4ALK; lacking amino acids 196-202) as search model (Schiebel et al. (2012), Structure 20:802-13). For PT173, the fully refined CG400549-I structure was used as a template for molecular replacement. To avoid model bias, $R_{free}$ flags were assigned in thin resolution shells (CG400549-I and -II) or copied from the search model (for PT173). The final structures were obtained by several alternative cycles of model building in Coot (Emsley et al. (2004) Coot: model-building tools for molecular graphics. Acta Crystallogr. D Biol. Crystallogr. 60:2126-32) and refinement in Refmac 5 (CG400549-bound structures) (Murshudov et al. (1997) Refinement of macromolecular structures by the maximum-likelihood method. Acta Crystallogr. D Biol. Crystallogr. 53:240-55) or Phenix (PT173) (Adams et al. (2010) PHENIX: a comprehensive Python-based system for macromolecular structure solution. Acta Crystallogr. D Biol. Crystallogr. 66:213-21), respectively (including noncrystallographic symmetry (PT173, CG400549-II) and TLS refinement (Painter et al. (2006) TLSMD web server for the generation of multi-group TLS models. J. Appl. Crystallogr. 39:109-11). Cofactors and inhibitors could be unambiguously assigned based on the $2F_o$-$F_c$ and $F_o$-$F_c$ electron density maps.

Crystals of the CG400549 and PT166 ternary ecFabI complexes were cryo-protected using the corresponding mother liquor supplemented by 25 or 30 v/v % ethylene glycol, respectively. Using a Pilatus 6M detector, diffraction data were collected at MX beamline 14.1 of the BESSY II synchrotron ($\lambda$=0.918 Å, T=100 K) and at beamline 23-1 of the European Synchrotron Radiation Facility ($\lambda$=1.064 Å, T=100 K), integrated using XDSAPP (Krug et al. (2012)

XDSAPP: a graphical user interface for the convenient processing of diffraction data using XDS. J. Appl. Crystallogr. 45:568-72), and scaled with Scala. Initial phases were determined by molecular replacement in Phaser with previously published ecFabI structure (PDB code 1QSG) as the search model (Stewart et al. (1999) Structural basis and mechanism of enoyl reductase inhibition by triclosan. J. Mol. Biol. 290:859-65). Model building in Coot and refinement using Refmac 5 (including TLS refinement) yielded the final structure. The amino acids 193 to 209/211 were not modeled due to only partial and very weak electron density for the two monomers in the asymmetric unit. In addition, the CG400549 electron density in subunit B was sufficient for model building but inferior compared with monomer A. Dictionaries for the cofactors and inhibitors of the S. aureus and E. coli FabI structures were computed using Grade (Smart et al. (2011) Grade. Global Phasing Ltd., Cambridge, UK; Bruno et al. (2004) Retrieval of crystallographically-derived molecular geometry information. J. Chem. Inf. Comput. Sci. 44:2133-44).

bpFabI crystals were cryo-cooled in cryo-protectant containing 25 v/v % glycerol in the mother liquor. Data collection was performed at an in-house x-ray generator (Micro-Max-007 HF, Rigaku) at a wavelength of 1.54 Å and recorded with an imaging plate detector (R-Axis HTC, Rigaku). Data were integrated with Imosflm and scaled in Scala. Molecular replacement was performed in Phaser using the PDB entry 3EK2 as a template. For refinement in Refmac and finally Phenix TLS parameters were created using the TLSMD server (Painter et al. (2006), J. Appl. Crystallogr. 39:109-11) and a library file supplying restraints for the cofactor and inhibitor was generated by the Prodrg server (Schuttelkopf et al. (2004) PRODRG: a tool for high-throughput crystallography of protein-ligand complexes. Acta Crystallogr. D Biol. Crystallogr. 60:1355-63). The structure was refined until convergence ($R/R_{free}$=14/16%) and validated using the Molprobity server (Chen et al. (2010) MolProbity: all-atom structure validation for macromolecular crystallography. Acta Crystallogr. D Biol. Crystallogr. 66:12-21).

To avoid model bias, omit maps were calculated prior to inclusion of cofactors and inhibitors. Data collection and refinement statistics are given in Schiebel et al., *The Journal of Biological Chemistry*, Jun. 6, 2014, 289(23):15987-16005, supplemental Table S1 (saFabI) and supplemental Table S2 (ecFabI and bpFabI). Distances and angles were measured for all subunits of the asymmetric unit and are given as mean values ±S.D. Structural figures were prepared using PyMOL (DeLano, W. L. (2002) The PyMOL Molecular Graphics System, DeLano Scientific LLC, San Carlos, Calif.).

The structure factors and coordinates of the different FabI structures have been deposited in the Protein Data Bank with the PDB entry codes 4CUZ (saFabI-NADPH-PT173), 4CV1 (saFabI-NADPH-CG400549-I), 4CV0 (saFabI-NADPHCG400549-II), 4CV2 (ecFabI-NADH-CG400549), 4CV3 (ecFabI-NADH-PT166), and 4BKU (bpFabI-NAD+-PT155).

Inhibition Kinetics—

Kinetics were performed on a Cary 100 spectrophotometer (Varian) at 20° C. Reaction velocities were measured by monitoring the oxidation of NAD(P)H to NAD(P)$^+$ at 340 nm ($\epsilon$ =6220 M$^{-1}$ cm$^{-1}$). For saFabI, the reaction mixture was identical to that described previously for progress curve experiments (Schiebel et al. (2012). Structure 20:802-13). For ecFabI, the final reaction mixture contained ecFabI (75 nM), trans-2-butenoyl-CoA (800 µM; Sigma and Advent Bio), NADH (300 µM; Sigma), NAD$^+$ (400 µM; Sigma), and inhibitor (2 v/v % DMSO) in 50 mM potassium phosphate, pH 7.5, 150 mM NaCl, 8 v/v % glycerol. For InhA, the final reaction mixture contained InhA (100 nM), trans-2-octenoyl-CoA (200 µM), NADH (250 µM), NAD$^+$ (200 µM), and inhibitor (2 v/v % DMSO) in 30 mM PIPES, pH 6.8, 150 mM NaCl, 1 mM EDTA, 8 v/v % glycerol. The resulting curves were fit to the Morrison and Walsh integrated rate equation (Equation 1) (Morrison et al. (1988) The behavior and significance of slow-binding enzyme inhibitors. Adv. Enzymol. Relat. Areas Mol. Biol. 61:201-301). $K_i^{app}$ was determined using the standard isotherm equation (Equation 2) or Morrison quadratic equation for tight-binding inhibitors (Equation 3) (Morrison, J. F. (1969) Kinetics of the reversible inhibition of enzyme-catalysed reactions by tight-binding inhibitors. Biochim. Biophys. Acta 185:269-86). For the pyridones, the $K_i$ was extracted from $K_i^{app}$ using Equation 4, where $K_S$ and $K_{NAD(P)H}$ values are rationally derived estimates for the real values provided in supplemental Table S3 in Schiebel et al., *The Journal of Biological Chemistry*, Jun. 6, 2014, 289(23):15987-16005 or Chang et al. (2013). Biochemistry 52, 4217-28.

$$A_t = A_0 - v_s t - (v_i - v_s) \cdot \frac{1 - e^{-k_{obs}t}}{k_{obs}} \quad \text{(Eq.1)}$$

$A_t$ and $A_0$ are the absorbance at time t and time 0; $v_i$ and $v_s$ are the initial and steady-state velocities, and $k_{obs}$ is the pseudo-first order rate constant for the approach to steady state.

$$\frac{v_i}{v_u} = \frac{1}{1 + \frac{[I]}{K_i^{app}}} \quad \text{(Eq.2)}$$

$v_u$ is the control, uninhibited velocity, and $K_i^{app}$ is the IC50 value.

$$\frac{v_i}{v_u} = 1 - \frac{([E]_T + [I]_T + K_i^{app}) - \sqrt{([E]_T + [I]_T + K_i^{app})^2 - 4[E]_T[I]_T}}{2[E]_T} \quad \text{(Eq.3)}$$

$[E]_T$ and $[I]_T$ are the total enzyme and inhibitor concentrations, respectively.

$$K_i^{app} = K_i \left(1 + \frac{[S]}{K_S} + \frac{K_{NAD(P)H}}{[NAD(P)H]}\right) \quad \text{(Eq.4)}$$

$K_S$ and $K_{NAD(P)H}$ are the respective dissociation rate constants for the enoyl-CoA substrate and NAD(P)H.

For the jump dilution assay, 10 µM saFabI, 15 µM inhibitor, and 500 µM NADPH were preincubated overnight at room temperature followed by a 1:200 dilution into reaction buffer (50 mM potassium phosphate, pH 7.5, 150 mM NaCl, 1 M potassium glutamate, 8 v/v % glycerol) containing 1.5 mM trans-2-butenoyl-CoA and 350 µM NADPH. The resulting progress curve was fitted to Equation 1. All curve fitting was performed using KaleidaGraph Version 4.1.

Thermal Shift Assay

ThermoFluor experiments were carried out in 96-well plates (Concord) using the CFX96 Real Time PCR Detection System and C1000 Thermal Cycler (Bio-Rad), as described previously (Chang et al. (2013). Biochemistry 52, 4217-4228).

Docking Studies

A computational docking and scoring procedure was used to generate putative binding modes for all pyridone inhibitors investigated. The binding poses were generated with FlexX (BioSolveIT, Sankt Augustin, 2009), version 3.1.4 (Rarey et al. (1996) A fast flexible docking method using an incremental construction algorithm. J. Mol. Biol. 261:470-89), and rescored with DrugScore$^X$ (G. Neudert and G. Klebe, University of Marburg, 2008), version 0.21, which builds on DrugScore and utilizes the DrugScore$^{CSD}$ potentials (Velec et al. (2005) DrugScore(CSD)-knowledge-based scoring function derived from small molecule crystal data with superior recognition rate of near-native ligand poses and better affinity prediction. J. Med. Chem. 48:6296-303; Gohlke et al. (2000) Knowledge-based scoring function to predict protein-ligand interactions. J. Mol. Biol. 295:337-56; Neudert et al. (2011) DSX: a knowledge-based scoring function for the assessment of protein-ligand complexes. J. Chem. Inf. Model. 51:2731-45). To account for the flexibility of the substrate-binding loop, all inhibitors were docked into subunits A and C of the saFabI CG400549-I structure, which represent the two experimentally observed states (for details see "Results"). The selection of the most likely binding pose and receptor was based on the DrugScore$^X$ score combined with visual inspection (supplemental FIG. S1 in Schiebel et al., *The Journal of Biological Chemistry*, Jun. 6, 2014, 289(23):15987-16005). A comparison with the available experimental binding modes revealed root mean square deviations below 1.1 Å for the 10 best ranked binding poses, with 0.7 Å (CG400549) and 0.8 Å (PT173) for the top ranked pose, respectively (supplemental FIG. S1, A and B in Schiebel et al., *The Journal of Biological Chemistry*, Jun. 6, 2014, 289(23):15987-16005). These re-/cross-docking experiments confirm the validity and reliability of the computational approach.

The inhibitors were setup with MOE (Chemical Computing Group, Montreal, 2010), version 2010.10 (Chemical Computing Group (2010) Molecular Operating Environment, Version 2010.10. Montreal, Quebec, Canada), and energetically minimized (Tripos force field) using SYBYL-X (Tripos, St. Louis, 2009), version 1.0 (Tripos (2009) SYBYL-X, Version 1.0. St. Louis, Mo.). NADPH was protonated within the saFabI environment using MOE. The saFabI CG400549-I crystal structure was protonated in FlexX, and the binding site region was defined by NADPH and amino acids 93-99, 102, 121, 146-147, 154-157, 160, 164, 190-193, 195, 197-204, and 207. Water molecules within a radius of 6 Å around CG400549 were included during the docking procedure and treated as displaceable particles. FlexX was run in command line mode with a default docking procedure, followed by post-docking optimization. Root mean square deviations were calculated using fconv (G. Neudert and G. Klebe, University of Marburg, 2012), version 1.24 (Neudert et al. (2011) fconv: format conversion, manipulation and feature computation of molecular data. Bioinformatics 27, 1021-1022).

Determination of MIC

Values MIC values were determined with the microbroth dilution assay according to the Clinical and Laboratory Standards Institute methods for antimicrobial susceptibility tests for aerobically growing bacteria (Clinical and Laboratory Standards Institute (2006) Approved Standard M7-A5, 6th Ed., Clinical and Laboratory Standards Institute, Wayne, Pa.).

Selection for Resistance

*S. aureus* RN4220 was grown at 37° C. in Mueller-Hinton (MH) broth to late log phase ($A_{600}$=1.2). 200 µl of culture was plated on MH agar containing PT166 (2 µg/ml; 5×MIC). After 48 h, five resistant colonies were randomly selected, and their phenotypes were confirmed by re-growth on the same medium containing PT166. The genomic DNA was extracted and purified using the Quick g-DNA Mini Prep kit (ZYMO Research). The *S. aureus* fabI genes from the PT166-resistant mutants were characterized by double-stranded nucleotide sequencing of PCR products using the following primers: saFabI forward (5'-CTAATTAG-GCATATG TTAAATCTTGAAAACAAAACG-3') and saFabI reverse (5'-GTAAGTGCTCGAGTT ATTTAATT-GCGTGGAATCC-3'). Sequencing reactions were performed with the ABI PRISM BigDye Terminator Cycle Sequencing Ready Reaction kit (Applied Biosystems, Foster City, Calif.), and sequencing data were obtained using an Applied Biosystems 3730 DNA sequencer.

In Vivo Pharmacokinetics

Pharmacokinetic (PK) studies were conducted in female ICR mice via intraperitoneal administration of PT04 (200 mg/kg dose) or PT166 (100 mg/kg dose) in a vehicle of 40 v/v % PEG 400, 40 v/v % EtOH, 20 v/v % $H_2O$. Blood samples were collected from each animal at eight time points (5, 15, and 30 min and 1, 2, 4, 8, and 24 h post-injection). Three mice were sampled per time point. Plasma concentrations for each sample were measured by LC/MS/MS, and PK parameters were calculated with WinNonlin (Pharsight Corp., Mountain View, Calif.).

In Vivo Efficacy

Antibacterial efficacy of 5-hexyl-2-phenoxyphenol (PT04) and PT166 (Table 1) was evaluated in a neutropenic mouse thigh infection model. Six-week-old male Swiss Webster mice weighing 23-27 g were rendered neutropenic by intraperitoneal injection of cyclophosphamide 4 days (150 mg/kg) and 1 day (100 mg/kg) prior to infection. Previous studies have shown that this can produce severe neutropenia in mice for at least 5 days (Gerber et al. (1982) Selection of aminoglycoside-resistant variants of *Pseudomonas aeruginosa* in an in vivo model. J. Infect. Dis. 146:691-7).

MRSA strain BAA1762 was cultured in MH broth to mid-log phase ($A_{600}$=0.4; 3×10$^8$ cfu/ml) and harvested by centrifugation. Cell pellets were resuspended in freshly sterilized heart infusion (BHI) broth to a final inoculum of 1×10$^7$ cfu/ml. 50 µl of this suspension (5×10$^5$ cfu) was injected intramuscularly into the left thigh of each mouse, and 50 µl of BHI broth was injected into the right thigh as control. The drug was administered by subcutaneous injection at 1 and 12 h post-infection (100 mg/kg dose per injection). Mice were euthanized 24 h post-infection. Each thigh muscle was subsequently collected and homogenized in saline containing 10 w/v % BHI broth. The bacterial load was determined by counting colony-forming units of serial dilutions plated on MH sheep blood agar.

For in vivo efficacy and PK studies, all animals were maintained in accordance with criteria set by the American Association for Accreditation of Laboratory Animal Care. This study was approved by the Institutional Animal Care and Use Committee (IACUC) at Stony Brook University.

Results
CG400549 and Related 2-Pyridones Selectively Inhibit Growth of *S. aureus*

The 2-pyridone CG400549 exhibits potent activity against *S. aureus* in contrast to many other bacteria such as *E. coli, Listeria monocytogenes, Helicobacter pylori*, and *Pseudomonas aeruginosa* (Yum et al. (2007), In vitro activities of CG400549, a novel FabI inhibitor, against recently isolated clinical staphylococcal strains in Korea. Antimicrob. Agents Chemother. 51:2591-3). This disparity was confirmed by comparing growth inhibition of *S. aureus* and *E. coli* with various 2-pyridone inhibitors (Tables 1 and 2). In contrast to the *Staphylococcus*-specific 2-pyridones, diphenyl ethers are active against a broader spectrum of microorganisms. It is therefore important to elucidate whether the narrow spectrum behavior of 2-pyridones can be attributed to FabI-specific differences between species and why these compounds behave differently compared with the structurally similar diphenyl ethers.

Figure 2A:
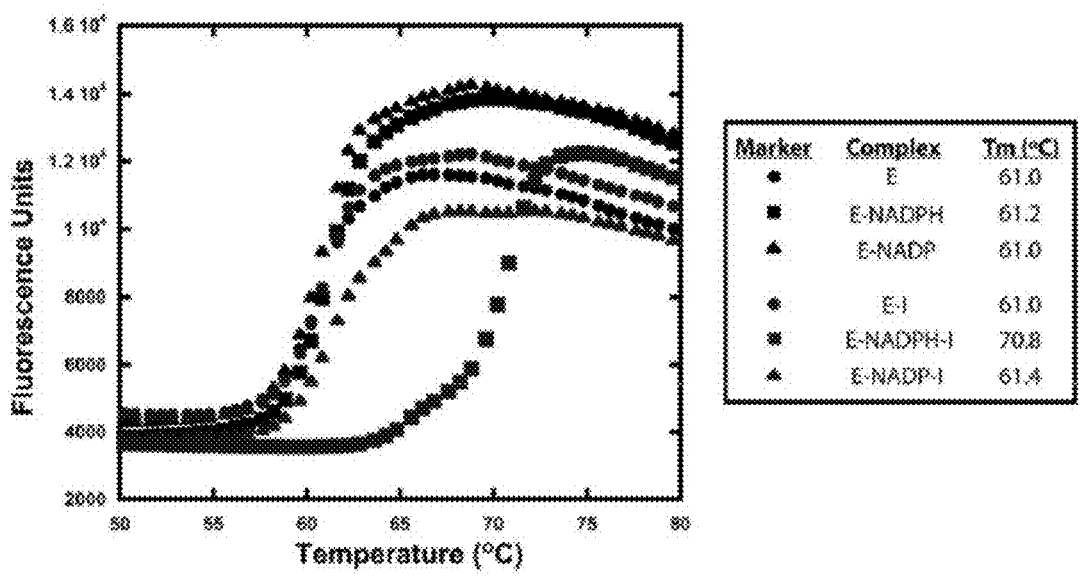
FIG. 2A is a graph showing different mechanisms of saFabI inhibition. Thermal shift analyses of saFabI bound to NADPH, NADP$^+$, and/or inhibitor (CG400549). The measurement variability is approximately ±0.2° C.
Figure 2B:
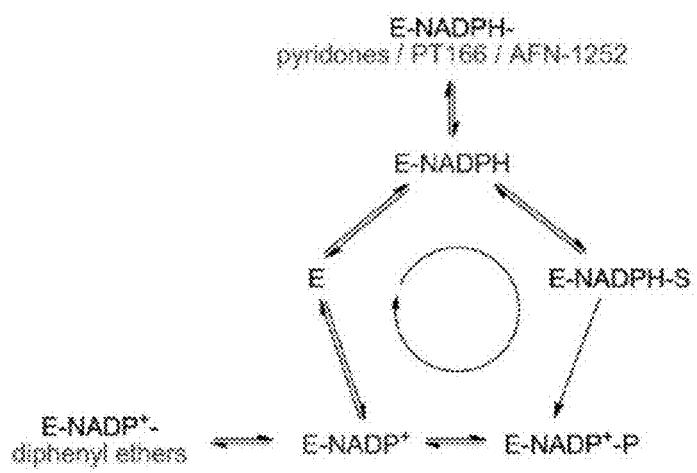
FIG. 2B. Distinct mechanisms of saFabI inhibition. Based on recent kinetic and structural results, it was reasoned that the enzyme binds NADPH first followed by the substrate. In contrast to diphenyl ethers, which bind to the enzyme-product complex generated via catalysis (E-NADP$^+$, pyridone compounds, PT166 (supplemental FIG. S2 in Schiebel et al. "Rational Design of Broad Spectrum Antibacterial Activity Based on a Clinically Relevant Enoyl-Acyl Carrier Protein (ACP) Reductase Inhibitor," *The Journal of Biological Chemistry*, (2014), 289(23):15987-16005) and AFN-1252, preferentially inhibit saFabI at the enzyme-substrate complex state (E-NADPH.
Figure 2C:
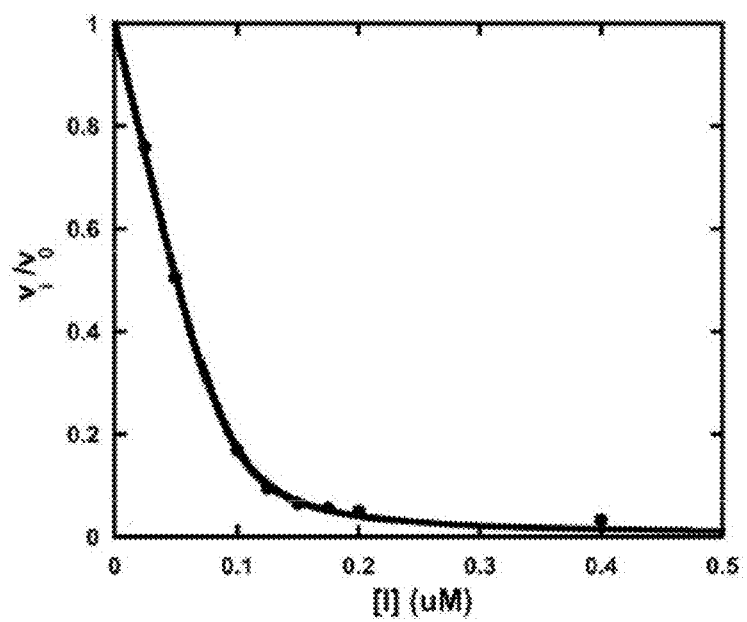
FIG. 2C. Representative plot of fractional velocity ($v/v_0$) as a function of inhibitor concentration for a potent pyridone (CG400549, in this example). The shape is characteristic of tight-binding inhibition. The best fit curve to the Morrison quadratic equation (Equation 3) yields $K_i^{app}$=4.73±0.50 nM and $[E]_T$=92.73±2.52 nM ($R^2$=0.99).

In Contrast to the Diphenyl Ethers, 2-Pyridones Bind to the E-NADPH Complex and Exhibit Fast-on Kinetics It was found that diphenyl ethers bind exclusively to the E-NADP$^+$ enzyme-product complex generated via catalysis (Chang et al., Biochemistry 52:4217-28). Despite the obvious structural similarity between pyridone and diphenyl ether inhibitors (FIG. 1), thermal shift assays revealed preferable binding of pyridones to the E-NADPH complex (FIG. 2A and Table 1). Thus, these inhibitors are uncompetitive with respect to NADPH but competitive with respect to the acyl substrate (FIG. 2B). Kinetic studies confirmed this pattern of saFabI inhibition, showing enhanced inhibition with increasing concentrations of NADPH and decreasing concentrations of the substrate trans-2-octenoyl-CoA used in the assay (data not shown). Moreover, pyridones were co-crystallize with saFabI using the reduced form of the cofactor. Accordingly, the saFabI target can be productively inhibited at two different stages of the catalytic cycle, as exemplified by pyridones and diphenyl ethers (FIG. 2B). This finding is of particular importance for the development of improved FabI inhibitors because most known scaffolds bind adjacent to the nicotinamide ring of the cofactor (Lu et al. (2008) Inhibitors of FabI, an enzyme drug target in the bacterial fatty acid biosynthesis pathway. Acc. Chem. Res. 41:11-20). The absence or presence of a buried positive charge in the E-NADPH versus E-NADP$^+$ binary complex likely will have a critical influence on the true affinity of potential inhibitors (Bissantz et al. (2010) A medicinal chemist's guide to molecular interactions. J. Med. Chem. 53:5061-84). However, the relative potencies of inhibitors with different modes of action are highly dependent on the experimental assay condition (see below). Because NADPH binds with higher affinity to the enzyme compared with NADP$^+$, the E-NADPH binary complex exists at a higher population for most experimental assay conditions (Xu et al. (2008). Mechanism and inhibition of saFabI, the enoyl reductase from *Staphylococcus aureus*. Biochemistry 47:4228-36; Chang et al. (2013). Biochemistry 52, 4217-4228). Thus, even though CG400549 exhibits weaker true thermodynamic affinity ($K_i$) than most diphenyl ethers, its apparent inhibition constant ($K_i^{app}$) is much more potent in the standard enzyme assay (Table 1), requiring classical tight binding analysis (FIG. 2C).

Figure 2D:
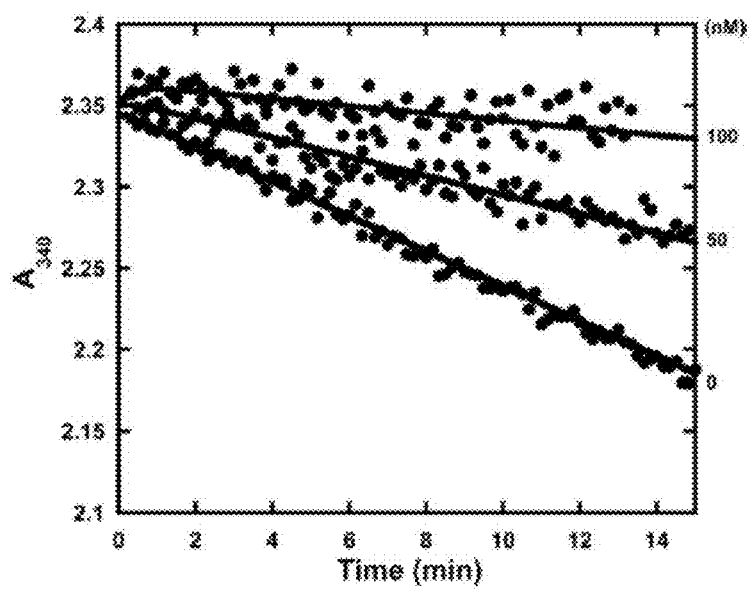
FIG. 2D. Representative set of forward progress curves with pyridone-based inhibitors of saFabI. The plot depicts rapid-onset inhibition at different PT173 concentrations.
Figure 2E:
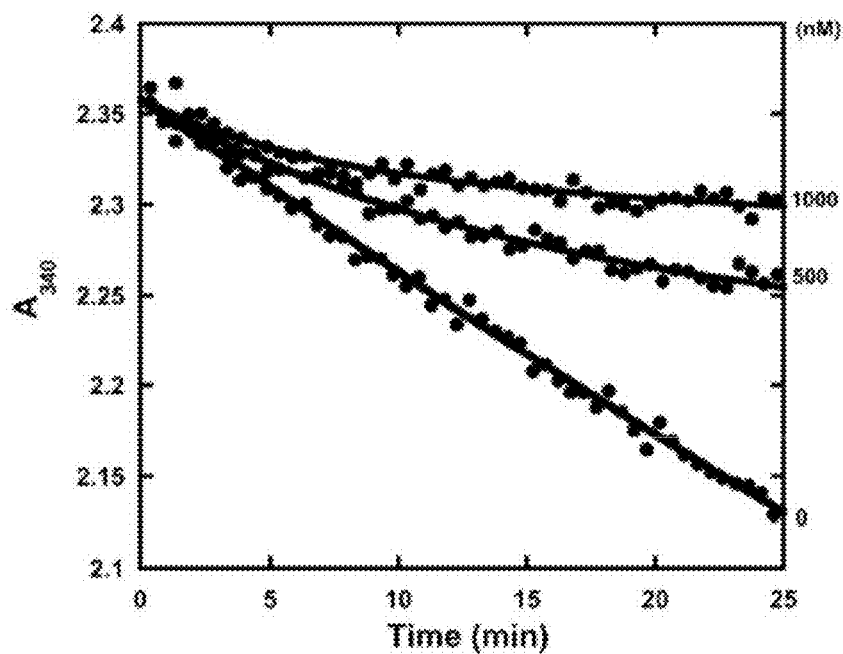
FIG. 2E. As a reference, this plot illustrates the slow-onset inhibition of saFabI by the diphenyl ether PT04. Note the clear observation of curvature that is absent in D.
Figure 2F:
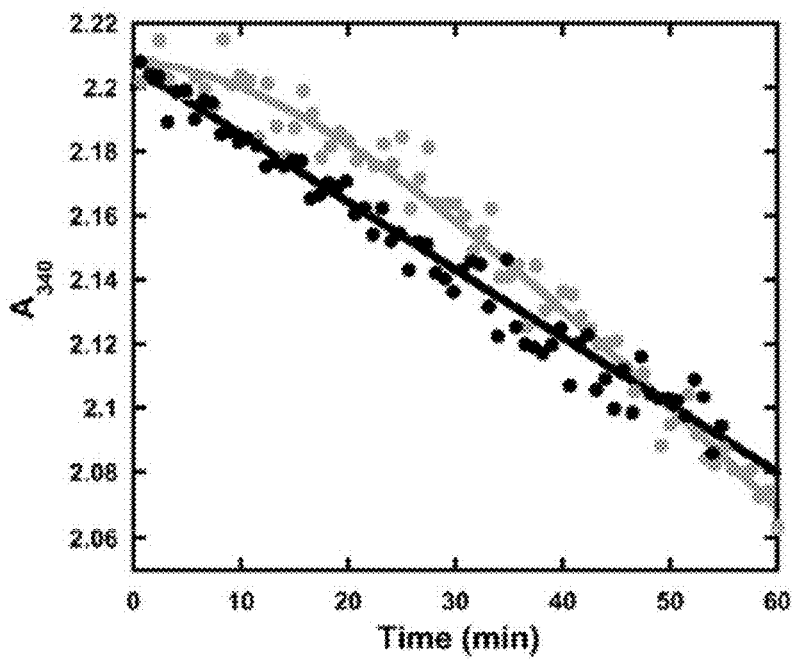
FIG. 2F. Jump dilution curve for CG400549 following preincubation with NADPH and saFabI. The jump dilution curve for the slow off diphenyl ether inhibitor PT52 following preincubation with NADP$^+$ and saFabI is shown as reference (full recovery of activity; $t_R$=30 min, where $t_R$ is the residence time). The lack of curvature for CG400549 is consistent with rapid off kinetics.

Pyridone and diphenyl ether saFabI inhibitors also differ with respect to their apparent association and dissociation kinetics. Diphenyl ethers exhibit slow binding kinetics and bind with long residence times to their target (FIGS. 2, E and F) (Schiebel et al. (2012). Structure 20, 802-13; Chang et al. (2013). Biochemistry 52, 4217-28). In contrast, progress curves of saFabI in the presence of pyridones are linear, displaying apparent rapid-onset kinetics (FIG. 2D). This is likely attributed to the higher population of E-NADPH compared with E-NADP$^+$. In fact, an estimate of the actual association rate constant yields a value in the same range as for the diphenyl ethers (Chang et al. (2013). Biochemistry 52, 4217-4228). Moreover, the rapid appearance of activity following jump dilution is highly indicative of fast off kinetics (FIG. 2F). This is consistent with the weaker true thermodynamic affinity ($K_i$) of pyridones compared with diphenyl ethers. In other words, differences in $k_{off}$ are driven by $K_i$ rather than $k_{on}$.

Figure 3A:
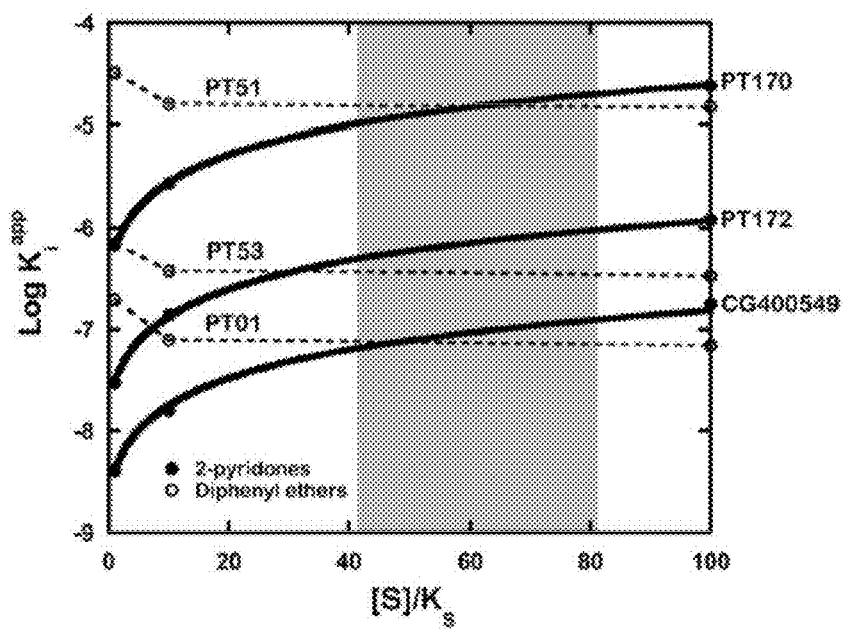
FIG. 3A is a graph showing rationalizing the in vitro cellular potency of competitive and uncompetitive FabI inhibitors. Relationship between acyl substrate concentration as a multiple of KS ([S]/KS) and the apparent affinity ($K_i^{app}$) of pyridones (PT170, PT172, and CG400549) and diphenyl ethers (PT51, PT53, and PT01) is illustrated. The plots are simulated based on $K_i$ values against saFabI (Table 1), the mechanism of inhibition shown in FIG. 2B, and the kinetic model described in Chang et al. (2013) Rational optimization of drug-target residence time: insights from inhibitor binding to the *Staphylococcus aureus* FabI enzyme-product complex. Biochemistry 52:4217-4228. The range of substrate concentration that best correlates relative $K_i^{app}$ to relative MIC for both classes of compounds is shaded in gray.
Figure 3B:
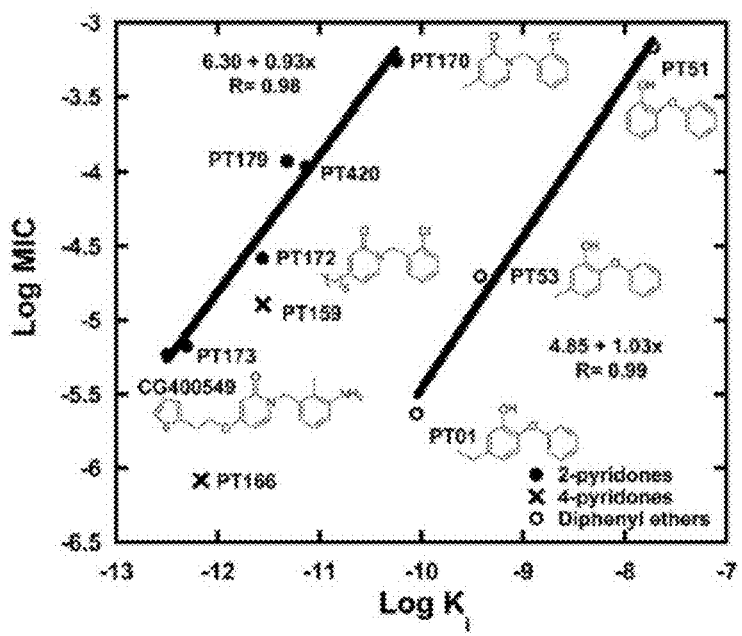
FIG. 3B. Double logarithmic plot depicts a strong linear correlation between $K_i$ of the overall ternary complex ($K_iX$ $K_{d,NADP(H)}$) and MIC for the 2-pyridone series (●) and diphenyl ethers (○). Points corresponding to 4-pyridones (X) are superimposed. Note that in this plot, the MIC for PT170 was assumed to be 550 μM, which is a lower limit estimate.
Figure 3C:
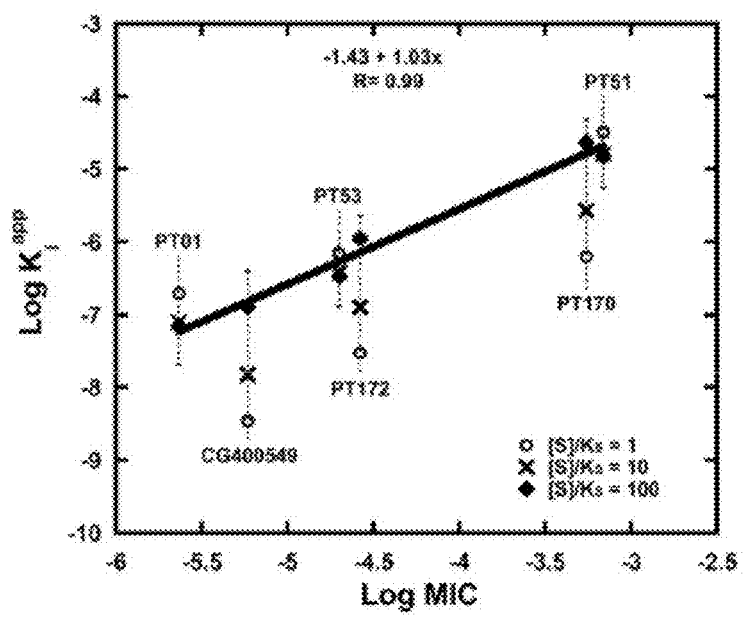
FIG. 3C. This double logarithmic plot of $K_i^{app}$ and MIC illustrates how 2-pyridones and diphenyl ethers can lie on the same linear correlation at the estimated substrate concentration [S] in the cell. Data points correspond to inhibitor $K_i^{app}$ values at [S]/$K_S$ of 1 (○), 10 (X) and 100 (♦). The linear correlation for points corresponding to [S]/$K_S$=100 is depicted.

The mode of action can have significant implications for cell growth inhibition. In open systems, substrate accumulation may eventually diminish the effect of competitive inhibitors (Westley et al. (1996) Enzyme inhibition in open systems. Superiority of uncompetitive agents. J. Biol. Chem. 271:5347-52). Therefore, it is important to consider the relationship between substrate concentration and $K_i^{app}$ (FIG. 3A). In FIG. 3B, a linear correlation was observed in the double logarithmic plot of $K_1$ versus MIC for both 2-pyridones and diphenyl ethers, consistent with on-target effects. However, 100-fold higher overall ternary complex affinity ($K_i$X $K_{d,NADP(H)}$) is needed for 2-pyridones to obtain a similar cellular potency as diphenyl ethers. Although this could be due to differences in cell permeability, this observation may also arise from substrate accumulation. The MIC is a thermodynamic parameter that is essentially equivalent to a physiological apparent inhibition constant ($K_i^{app}$). For competitive inhibitors, such as the pyridone compounds, the presence of high substrate concentrations may weaken the apparent affinity. Alternatively, because the rate of substrate reduction ($k_{cat}$=40 min$^{-1}$) will increase as substrate concentration increases ($K_S$=0.75 mM), a higher proportion of E-NADP$^+$ is formed, which can bind to the uncompetitive diphenyl ether compounds. At a substrate concentration range of 40-80 times $K_S$, the relative $K_i^{app}$ values are very predictive of the pattern of MIC values for both 2-pyridones and diphenyl ethers (FIG. 3C). This allows translation to $K_i$ to $K_i^{app}$ values that are readily compared despite different modes of action. The true level of substrate accumulation in the cell is likely to be lower than predicted by this calculation. The cell contains longer chain substrates with faster turnover rates (Schiebel et al. (2012). Structure 20, 802-813), which will increase the apparent affinity of diphenyl ethers. For instance, if an average FabI turnover rate of 400 min$^{-1}$ is assumed, the predicted substrate concentration range would be 4-8 times $K_S$, which is a much more reasonable estimate.

The utility of a scaffold for lead optimization is related, in part, to its intrinsic potency, herein defined as the potency of a relatively unmodified scaffold, i.e. the starting point that determines how much affinity optimization is needed. For instance, PT170 and PT53 represent relatively unmodified 2-pyridone and diphenyl ether scaffolds, respectively (Table 1). The accumulation of substrate likely weakens the intrinsic potency of the competitive 2-pyridone scaffold relative to the uncompetitive diphenyl ether scaffold by more than 20-fold (FIG. 3A). Thus, further optimization of 2-pyridones is needed to achieve potent cellular activity. As demonstrated herein, such optimization is much more readily attained in the case of saFabI compared with other FabI homologues, providing the rationale for the narrow spectrum activity of CG400549 and related 2-pyridone compounds.

Clinical Candidate CG400549 Interacts Tightly with saFabI

Figure 4A:
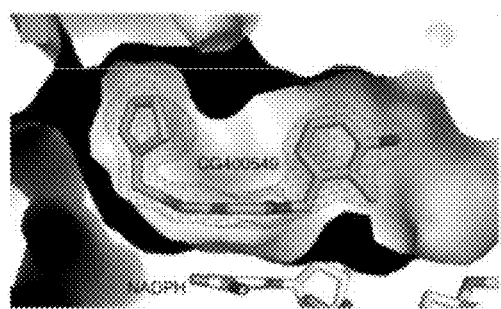
FIG. 4A is a depiction of molecular interactions of saFabI with the pyridone inhibitor CG400549. 2F$_o$-F$_c$ omit map for CG400549 bound to saFabI. According to the omit map (shown as mesh at 1σ), CG400549 unambiguously binds to the hydrophobic saFabI active site pocket. An intersection of the CG400549-I structure (subunit G, depicted in gray surface representation) provides insight into this cavity.
Figure 4B:
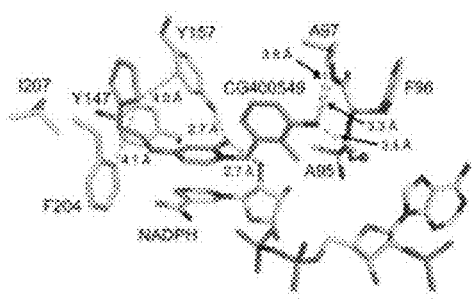
FIG. 4B. Binding mode of CG400549 in complex with saFabI and NADPH. Interactions between inhibitor, cofactor, and protein are highlighted by dashed lines. Selected residues of the saFabI binding pocket are shown as gray sticks (CG400549-I structure, subunit G).

CG400549 binds with high affinity ($K_i$=1.27 nM) to saFabI (Table 1). To provide insight into the underlying molecular interactions, two different saFabI-NADPH-CG400549 ternary complex structures were solved (CG400549-I and CG400549-II, respectively; unless stated otherwise, the CG400549-I structure was used for the following analyses; see also supplemental Table S1 of Schiebel et al., *The Journal of Biological Chemistry*, Jun. 6, 2014, 289(23):15987-16005. Based on the associated $2F_o$-$F_c$ omit maps, the binding mode of CG400549 was unambiguously revealed (FIG. 4A), which enables the formation of two central hydrogen bonds of the pyridone carbonyl oxygen with the Tyr-157 hydroxyl and the NADPH nicotinamide ribose 2'-OH at distances of 2.74±0.07 and 2.69±0.10 Å, respectively (FIG. 4B). Although reminiscent of interactions found for other inhibitor scaffolds (FIG. 1), these hydrogen bonds are 0.15 Å longer for pyridones in comparison with diphenyl ethers. This supports the hypothesis that diphenyl ethers bind to saFabI in their deprotonated form (Chang et al. (2013). Biochemistry 52, 4217-4228) leading to shorter charge-assisted hydrogen bonds. Additional long range hydrogen bonds are formed between the 3'-amino group of CG400549 (FIG. 1) and the main chain oxygen and nitrogen of Ala-97 at distances of 3.56±0.06 and 3.32±0.09 Å, respectively (FIG. 4B). Moreover, a water molecule is frequently bound between this B-ring $NH_2$ group and Ala-95 at 3.36±0.18 Å (FIG. 4B). Interestingly, Ala-97 is engaged in direct interactions to several potent saFabI inhibitors (FIG. 1). Triclosan and AFN-1252 form halogen and hydrogen bonds with Ala-97, respectively; and the amide group of MUT056399 was similarly suggested to interact with this residue (FIG. 1) (Schiebel et al. (2012). Structure 20, 802-813; Kaplan et al. (2012) Mode of action, in vitro activity, and in vivo efficacy of AFN-1252, a selective antistaphylococcal FabI inhibitor. Antimicrob. Agents Chemother. 56:5865-74; Gerusz et al. (2012) From triclosan toward the clinic: discovery of nonbiocidal, potent FabI inhibitors for the treatment of resistant bacteria. J. Med. Chem. 55:9914-28).

The unique 5-substituent of CG400549 (atoms of the diphenyl ether and pyridone scaffolds are numbered as indicated in the two lower boxes of FIG. 1) binds to a hydrophobic pocket with the thiophene moiety trapped between the three aromatic amino acids Tyr-147, Tyr-157, and Phe-204 (FIGS. 4, A and B). The side-on n-stacking interaction between Tyr-157 of the catalytic triad and the thiophene ring may contribute to the high affinity of CG400549 toward saFabI (Table 1). In particular, the thiophene sulfur interacts with the edge of Tyr-157 ($C_δ$) at a distance of 3.97±0.11 Å (62). A similar interaction is found between this sulfur atom and Phe-204 ($C_δ$) at 4.15±0.16 Å (FIG. 4B). Remarkably, among 13 CG400549-resistant *S. aureus* strains, 10 were characterized by a single F204L mutation, whereas the residual three had no mutations in the fabi gene (Park et al. (2007) Antistaphylococcal activities of CG400549, a new bacterial enoyl-acyl carrier protein reductase (FabI) inhibitor. J. Antimicrob. Chemother. 60:568-74). In contrast, multiple resistance mutations are known for diphenyl ethers (Xu et al. (2008). Biochemistry 47:4228-36; Heath et al. (2000). Inhibition of the *Staphylococcus aureus* NADPH-dependent enoyl-acyl carrier protein reductase bytriclosan and hexachlorophene. J. Biol. Chem. 275:4654-9; Escaich et al. (2011) The MUT056399 inhibitor of FabI is a new antistaphylococcal compound. Antimicrob. Agents Chemother. 55:4692-7; Fan et al. (2002) Defining and combating the mechanisms of triclosan resistance in clinical isolates of *Staphylococcus aureus*. Antimicrob. Agents Chemother. 46:3343-7; Brenwald et al. (2003) Triclosan resistance in methicillin-resistant *Staphylococcus aureus* (MRSA). J. Hosp. Infect. 55:141-4). Accordingly, the Phe-204-thiophene interaction seems to be critical for the activity of CG400549.

Figure 4C:
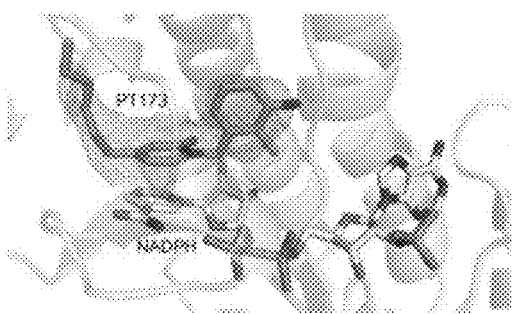
FIG. 4C. NCS-averaged $2F_o$-$F_c$ omit map for PT173. The omit map is shown at 1σ and reveals the presence of PT173. Subunit F of the PT173 structure is depicted in gray schematic representation.
Figure 4D:
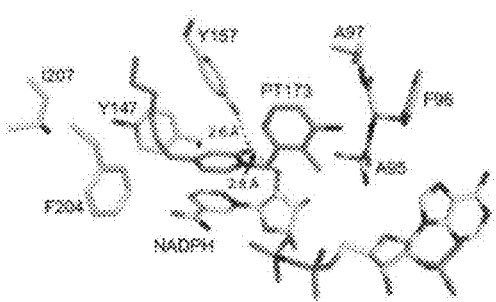
FIG. 4D. Experimental binding geometry of PT173. Selected residues of the saFabI-NADPH-PT173 structure (gray, subunit F) and the central hydrogen bonding network (dashed lines) are depicted.

In addition to the CG400549 structures, an saFabI structure in complex with NADPH and PT173 was solved, which displays a similar affinity toward saFabI as CG400549 ($K_i$=1.97 nM versus 1.27 nM) and contains a 5-hexyl group that mimics the natural enoyl-ACP substrate (FIG. 1) (Chang et al. (2013). Biochemistry 52:4217-28). Although the resolution was much lower (supplemental Table S1 of Schiebel et al., The Journal of Biological Chemistry, 2014, 289(23):15987-16005), clear density was observed for the cofactor and inhibitor (FIG. 4C). The binding mode of PT173 in the saFabI active site pocket is similar to CG400549, and the same central hydrogen bonding network between the inhibitor, cofactor, and Tyr-157 was observed (FIG. 4D).

Figure 5A:
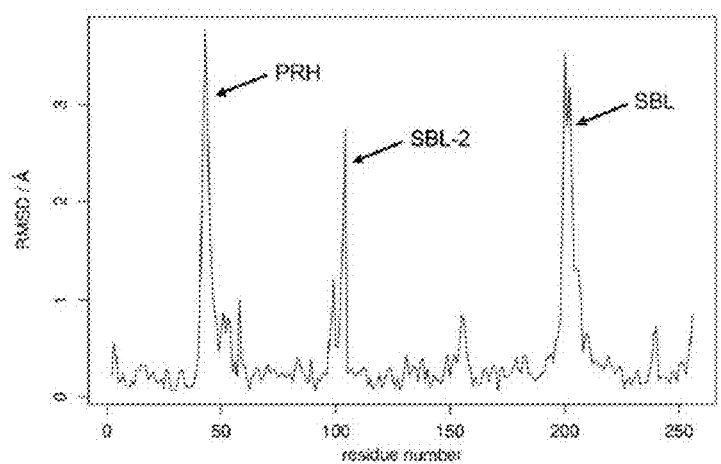
FIG. 5A is a depiction of structural variations between pyridone and diphenyl ether ternary complex structures. Structural differences between diphenyl ether and pyridone ternary complexes. Per residue root mean square deviation (RMSD) values between the triclosan-bound (PDB code 4ALI, subunit H) and CG400549-bound (CG400549-I, subunit C) structures were calculated using Theseus (Theobald et al. (2008) Accurate structural correlations from maximum likelihood superpositions. PLoS Comput. Biol. 4:e43) and are plotted against the residue number. The inhibitor-bound structures of these two scaffolds differ considerably in three regions of the protein (PRH=phosphate recognition helix α2; SBL-2=substrate-binding loop 2; SBL=substrate-binding loop).
Figure 5B:
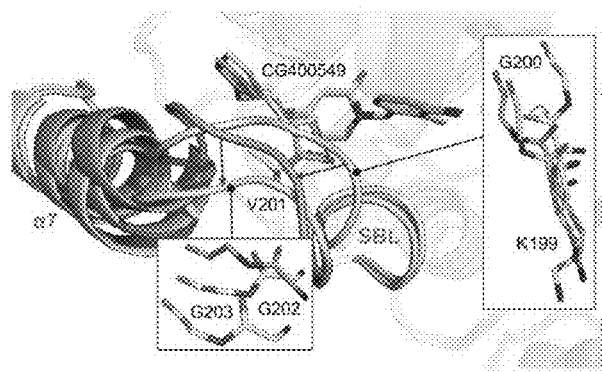
FIG. 5B. Conformational states of the SBL. The different subunits of the CG400549-I structures reveal two distinct states of the SBL and the attached helix α7. Compared with these conformations, the SBL is more closed in the triclosan-bound structure (shown in gray; PDB code 4ALI, subunit H). Detailed views of the three different conformations are displayed in the insets. Arrow indicate the conformational changes from the closed to the open substrate binding loop states and highlight backbone flips.

Despite the relative success of CG400549, little is known about pyridone FabI inhibitors and their structure-activity relationships (SAR) (Tipparaju et al. (2008) Design and synthesis of 2-pyridones as novel inhibitors of the *Bacillus anthracis* enoyl-ACP reductase. Bioorg. Med. Chem. Lett. 18:3565-9; Kitagawa et al. (2007) 4-Pyridone derivatives as new inhibitors of bacterial enoyl-ACP reductase FabI. Bioorg. Med. Chem. 15:1106-16; Takahata et al. (2007) Discovery of 4-pyridone derivatives as specific inhibitors of enoyl-acyl carrier protein reductase (FabI) with antibacterial activity against *Staphylococcus aureus*. J. Antibiot. 60:123-8). Thus, a series of pyridone compounds were synthesized and their ability to inhibit saFabI was investigated (Table 1). To rationalize the SAR results, putative binding modes were generated for all investigated inhibitors using a validated docking procedure, which could reproduce the CG400549 and PT173 binding geometries with low root mean square deviations (0.71 and 0.83 Å, respectively) (supplemental FIG. S1 of Schiebel et al., *The Journal of Biological Chemistry*, Jun. 6, 2014, 289(23):15987-16005). Because of the lipophilic environment, bulky and hydrophobic substituents are preferred at the 5-position. Hence, PT170 is the least potent compound of the pyridone series. Replacing the 5-methyl group by a 5-hexyl group (PT172) leads to a 21-fold affinity enhancement, which is underlined by the favorable scores for the additional carbon atoms (supplemental FIG. S1 of Schiebel et al., *The Journal of Biological Chemistry*, Jun. 6, 2014, 289(23):15987-16005). Similar to the 2'-chloro substituent of PT172, the 2'-methyl group of PT171, which is also present in CG400549, increases affinity by a factor of 2 compared with the unsubstituted analogue PT179. In comparison with the 2'-Cl and 2'-Me groups, a 2'-CN substituent leads to decreased potency. Interestingly, the SAR at this position is different from diphenyl ethers for which 2'-cyano is the best substituent (Chang et al. (2013). Biochemistry 52, 4217-28). Pyridone 2'-substituents are predicted to bind in a similar orientation (supplemental FIG. S1 of Schiebel et al., The Journal of Biological Chemistry, 2014, 289(23):15987-16005) as observed for diphenyl ethers. The introduction of a 3'-amino group as present in CG400549 and PT173 further enhances the affinity of PT171 by a factor of 6, which highlights the energetically favorable character of the observed long range hydrogen bonds between those inhibitors and Ala-97 (FIG. 4B). Replacement of the PT173 5-hexyl group with the 5-substituent of CG400549 further improves the affinity of the drug candidate 1.5-fold and might be explained by the additional aromatic interactions observed.

saFabI Conformational States Differ Between Pyridone and Diphenyl Ether Ternary Complex Structures In accordance with the distinct kinetic behavior of pyridone and diphenyl ether inhibitors, considerable structural differences between the corresponding ternary complex structures were observed. A per-residue root mean square deviation plot reveals variations in mainly three regions of the protein (FIG. 5A), the two substrate-binding loops (SBL and SBL-2; residues 194-204 and 94-108) and the phosphate recognition helix α2 (residues 40-54), which confers the unique NADPH specificity to saFabI (Schiebel et al. (2012). Structure 20:802-13). Complete closure of the SBL has been proposed to constitute the rate-limiting step of slow binding FabI inhibition by diphenyl ethers (Lu et al. (2008). Acc. Chem. Res. 41:11-20). Indeed, more "open" SBL states were found in the saFabI-NADPH-CG400549 structures compared with the triclosan-bound structure (FIG. 5B). Most likely the observation of the open state can partially be attributed to steric interference between the thiophene moiety of CG400549 and the side chain of Val-201 in the SBL if it would adopt the completely "closed" state (FIG. 5B, gray). Hence, Val-201 is shifted by 2.9±0.1 Å into the more open CG400549-bound structure (FIG. 5B, cyan). Interestingly, some subunits of the CG400549-I structure reveal a second, even more open SBL state; the root mean square deviation increases from 1.6 to 2.0 Å compared with the triclosan-bound reference structure, with an additional shift in helix α7, which was previously identified to be very flexible prior to ligand binding (FIG. 5B, yellow) (Schiebel et al. (2012). Structure 20, 802-13). Both SBL conformations in the saFabI-NADPH-CG400549 complex seem to be energetically equally favorable due to the observation of subunits with both states in equilibrium. The more closed state is stabilized by a sulfate ion, which is bound to backbone amides of the SBL; this state differs from the completely closed triclosan-bound structure by a Lys-199 to Gly-200 backbone flip (FIG. 5B, right inset; $\psi_{K199}$ and $\varphi_{G200}$ change by 156° and 159°, respectively), which is observed for seven of the eight CG400549-I monomers and might also be responsible for the opening movement. An additional shift of residues 202-208 with extensive variations for Gly-202 and Gly-203 leads to the most open form (FIG. 5B, left inset), which is related to the conformation observed for the AFN-1252 structure (Kaplan et al. (2012)r. Antimicrob. Agents Chemother. 56:5865-74).

Figure 5C:
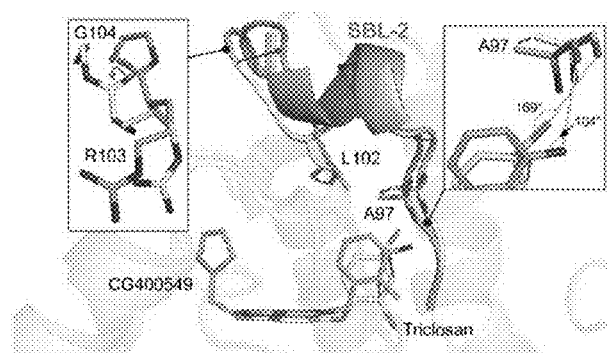
FIG. 5C. Conformational states of the SBL-2. Selected residues, the inhibitors, and the SBL-2 are shown for the CG400549-I (subunit A) and triclosan-bound structures (PDB code 4ALI, subunit H).

Similar to the SBL, a second loop that also contributes to the substrate binding pocket (SBL-2) was almost exclusively found to be in an open conformation in the saFabI-NADPHCG400549 structures (FIG. 5C, cyan). In contrast, alternative closed and open SBL-2 conformations for the diphenyl ether-bound structures were observed (Schiebel et al. (2012). Structure 20:802-13). An Arg-103 to Gly-104 backbone flip (FIG. 5C, left inset; $\psi_{R103}$ and $\varphi_{G104}$ change by 180° and 144°, respectively) clearly differentiates the two states. This flip is induced by (or induces) a 1.5±0.5 Å shift of Leu-102 out of the binding pocket, which in turn might be caused by (or causes) a considerable movement of the CG400549 B-ring toward this residue (FIG. 5C). The resulting differences between the pyridone and diphenyl ether binding poses (FIG. 5C) rationalize the varying SAR profiles at the 2'-position for both scaffolds and the success of the 3'-amino substituent in the case of pyridones. In particular, the 2'- and 3'-carbon atoms are relocated by 1.3±0.1 and 1.6±0.1 Å, respectively, which places the CG400549 3'-carbon at the position of the triclosan 4'-carbon. Consequently, 3'-pyridone and 4'-diphenyl ether substituents are ideally oriented to interact with the important anchor residue Ala-97. For instance, the triclosan 4'-Cl is halogen-bonded to the free electron pair of the Ala-97 carbonyl oxygen via the favorable linear geometry (FIG. 5C, right inset) (Schiebel et al. (2012). Structure 20:802-13; Bissantz et al. (2010). J. Med. Chem. 53:5061-84). To enable an equally favorable angular geometry for a hydrogen bond between the CG400549 3'-$NH_2$ group and Ala-97 along one amino hydrogen atom (Bissantz et al. (2010). J. Med. Chem. 53:5061-84), the Ala-97 carbonyl oxygen is shifted by 0.8±0.1 Å toward the B-ring of the inhibitor, which in turn approaches Ala-97 to reduce the interaction distance (FIG. 5C, right inset). As exemplified by these considerations, the exact knowledge of the different conformations that can be attained by a protein target is pivotal for the design of improved inhibitors.

Comparison of ecFabI and saFabI Inhibition by 2-Pyridones—

To determine whether the narrow spectrum behavior of CG400549 can be partly attributed to target-specific differences between species, the structures and inhibition kinetics of CG400549 with respect to *E. coli* and *S. aureus* FabI were obtained and compared. Indeed, CG400549 shows a 65-fold reduced affinity to ecFabI in comparison with saFabI (Tables 1 and 2), which translates into >64-fold lower antibacterial activity (Table 3). Nevertheless, the inhibitor clearly bound to the binary ecFabI-NADH complex with a similar binding geometry as observed for saFabI (FIGS. 6, A and B). However, in contrast to the related saFabI ternary complex, the substrate-binding loop and the attached helix α7, including residues 193-214, were found to be disordered in this ecFabI structure (FIG. 6A). Based on a comparison of these structures, it was proposed that the saFabI residues Val-201 and Ile-207, which are located in this region of the protein, contribute to the specificity of CG400549 toward saFabI. The more bulky Ile-200 and Met-206 ecFabI residues (corresponding to saFabI positions 201 and 207, respectively) restrict the available space for the large 5-substituents as present in CG400549 (FIG. 6B). Accordingly, the elongation of the 5-substituent in 5-ethyl-2-phenoxyphenol (PT01) to 5-hexyl-2-phenoxyphenol (PT04) does not enhance the affinity toward ecFabI (Table 2), whereas the affinity increases ~10-fold for saFabI. It was recently shown that these inhibitors are transition state analogues with the 5-substituent alkyl chain extending toward the fatty acyl binding channel (Chang et al. (2013). Biochemistry 52:4217-28). Although the $k_{cat}$ increases for longer enoyl substrates in the case of saFabI, it is similar among the different substrate chain lengths for *E. coli* and *F. tularensis* FabI, which both carry the V201I and I207M substitutions and are inhibited by PT01 and PT04 with similar potency (Schiebel et al. (2012). Structure 20, 802-13; Sivaraman et al. (2003). Biochemistry 42, 4406-4413; Lu et al. (2009) Slow-onset inhibition of the FabI enoyl reductase from *Francisella tularensis*: residence time and in vivo activity. ACS Chem. Biol. 4:221-31; Ward et al. (1999) Kinetic and structural characteristics of the inhibition of enoyl (acyl carrier protein) reductase by triclosan. Biochemistry 38:12514-25). Thus, the enlarged binding pocket of saFabI might partially explain the specific action of the comparatively bulky CG400549 and AFN-1252 clinical candidates (FIG. 1). Interestingly, the C terminus of the ecFabI monomer located on the opposite side of the homotetrameric protein (in particular, Met-256') seals this acyl binding cavity and likely restricts the side chain mobility of Met-206 (FIG. 6B). The resulting steric interference between the substrate-binding loop residues Met-206 and Ile-200 and the thiophene moiety of CG400549 presumably results in the experimentally observed enhanced mobility of this loop. In contrast, the C terminus of saFabI is shorter and lacks a residue corresponding to Met-256', thus enabling Ile-207 to move away from bulky 5-substituents. Consequently, important contacts between this inhibitor and the substrate-binding loop (e.g. with Phe204; see also FIG. 4B) are more readily attained, partially explaining the selectivity of CG400549 toward the saFabI homologue.

Figure 7:
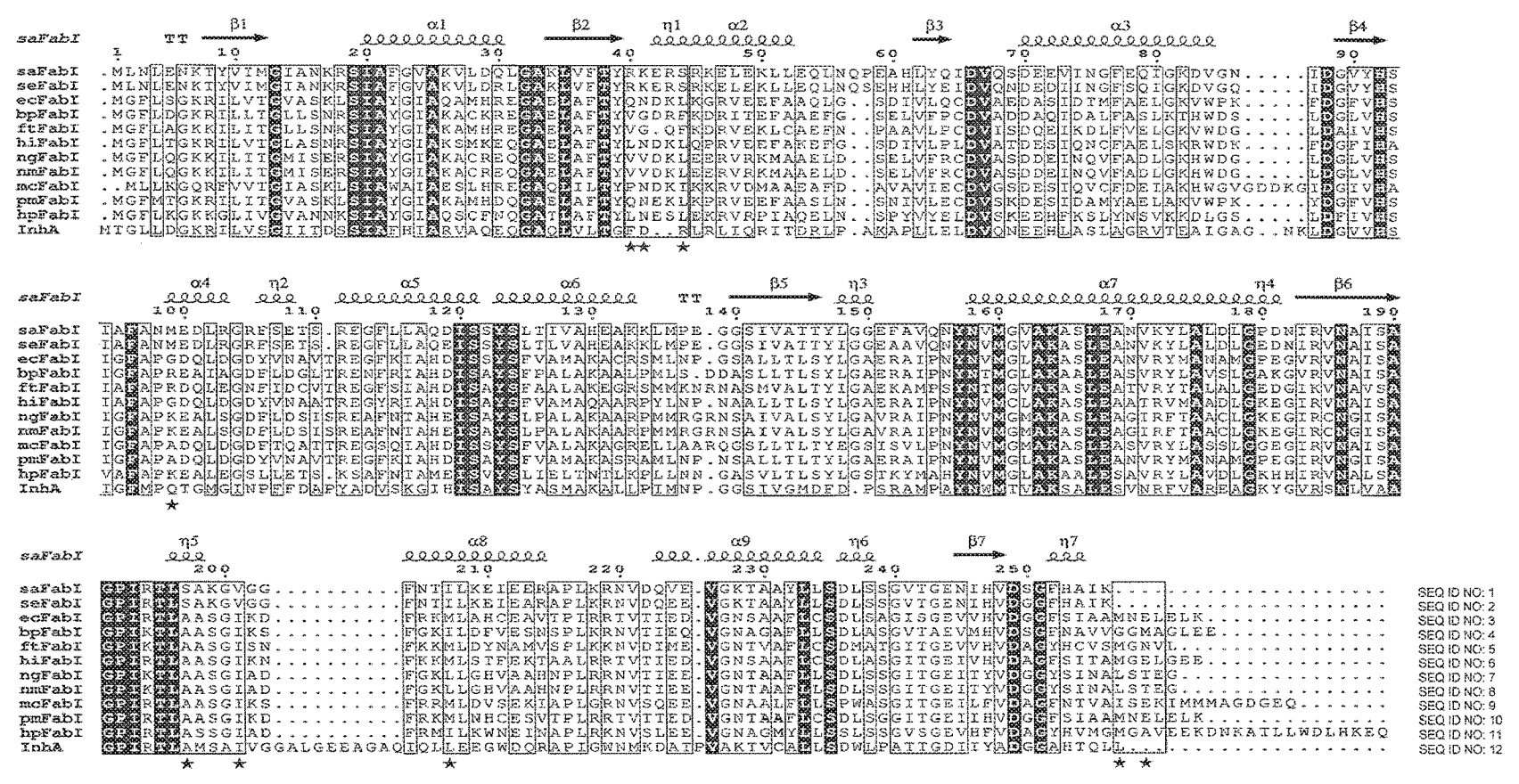

In line with the assumption that ecFabI is a good model for all FabIs insensitive to CG400549, an alignment of the FabI sequences from clinically relevant pathogens, which can be sensitive to FabI-specific inhibitors, reveals that staphylococcal FabIs differ fundamentally from classical FabI proteins such as ecFabI (FIG. 7). Most strikingly, all nonstaphylococcal FabIs included in this comparison contain extended C termini. A comparison of the available corresponding structures clearly shows that the four amino acids following the C-terminal Lys-256 of saFabI occlude the acyl-binding cavity for classical FabIs and thus restrict the available space for bulky 5-substituents (red box in FIG. 7). In particular, the additional large hydrophobic residues at position 257 (256 for ecFabI) or 259 (Met, Leu, and Be) will most likely interfere with bulky residues located at position 207, which thus cannot avoid the interference with large 5-substituents without the opening of the SBL (FIG. 6B). The length of the C terminus might therefore be an ideal indicator whether or not the corresponding FabI is sensitive to compounds such as CG400549 or AFN-1252. The presence of Val-201 instead of an isoleucine is an additional unique characteristic of FabIs sensitive to the more voluminous compounds and may facilitate the production of bulky branched-chain fatty acids abundant in *S. aureus* (FIGS. 6B and 7) (Schiebel et al. (2012). Structure 20:802-13).

In addition to the tolerance for bulky 5-substituents, hydrogen bonding interactions with Ala-97 seem to be particularly favorable in the case of saFabI and are exploited by the three drug candidates, as indicated by crystallographic and computational studies (FIG. 1) (Kaplan et al. (2012). Antimicrob. Agents Chemother. 56:5865-74; Gerusz et al. (2012). J. Med. Chem. 55:9914-28). In the case of CG400549, the more rigid Pro-96 of ecFabI (Asn-98 in the case of saFabI) slightly changes the orientation of the Ala-95 carbonyl (Ala-97 for saFabI) (FIG. 6B). This might explain the observed rotation in the B-ring of CG400549, which seems to be required for the maintenance of the hydrogen bond to this residue. Interestingly, this interaction is solvent-exposed (FIG. 6A) and less buried in ecFabI due to the presence of Gly-97, which corresponds to Met-99 in saFabI (FIG. 6B). This observation rationalizes why the 3'-amino substituent leads to a decrease in affinity in the case of ecFabI (Table 2) because solvent-exposed interactions tend to be energetically less favorable. Thus, other classical FabI proteins harbor a more hydrophilic residue at this position compared with saFabI (FIG. 7). Furthermore, treatment of *S. aureus* with AFN-1252, which also binds to the saFabI-NADPH complex and forms a hydrogen bond with Ala-97 (FIG. 1), predominantly selects for an M99T mutation, and it was recently suggested that this residue confers *S. aureus* selectivity to AFN-1252 (Kaplan et al. (2012). Antimicrob. Agents Chemother. 56:5865-74; Yao et al. (2013) Resistance to AFN-1252 arises from missense mutations in *Staphylococcus aureus* enoyl-acyl carrier protein reductase (FabI). J. Biol. Chem. 288:36261-71). Thus, the buried hydrogen bonding interaction with Ala-97 likely plays an important role in the selective affinity of CG400549 and AFN-1252 toward saFabI.

4-Pyridone PT166 is a Potent FabI Inhibitor with Extended Spectrum In Vitro Activity and In Vivo Efficacy Against *S. aureus*

In contrast to saFabI, strategies to optimize the binding affinity of 2-pyridones for ecFabI and related homologues may be limited due to the more constricted space in the binding crevice combined with the relatively low intrinsic potency of 2-pyridones compared with the diphenyl ether scaffold. Instead, to attain broad spectrum activity, a modified scaffold should be designed that possesses a higher intrinsic potency for all FabI homologues. One possibility is the replacement of the methylene bridge with an ether linkage, thereby changing the conformational preference prior to binding. The biologically active Ar-X-Ar conformation (Ar=aromatic ring, X=$CH_2$ or O, FIGS. 4 and 6) is more readily available for the bisaryl ether system thus leading to an entropic advantage upon binding (Brameld et al. (2008) Small molecule conformational preferences derived from crystal structure data. A medicinal chemistry focused analysis. J. Chem. Inf. Model. 48:1-24). This was implemented in the design of C-substituted 2-pyridone (in contrast, 2-pyridones such as CG400549 are substituted at the nitrogen atom) and 4-pyridone analogues. As expected, both prefer to bind in a ternary complex with NADPH (supplemental FIG. S2 of Schiebel et al., *The Journal of Biological Chemistry*, 2014, 289(23):15987-16005), thus preserving the 2-pyridone mode of action. Compared with the analogous N-substituted 2-pyridone PT179, the C-substituted 2-pyridone PT191 binds 10-fold less tightly to saFabI (Table 1). Although the enol form of PT191 displays a similar putative binding geometry as PT179 (supplemental FIG. S1 of Schiebel et al., *The Journal of Biological Chemistry*, 2014, 289(23):15987-16005) and more closely resembles the potent diphenyl ether PT04 (Chang et al. (2013). Biochemistry 52:4217-28; Tipparaju et al. (2008). Bioorg. Med. Chem. Lett. 18, 3565-3569), the increased desolvation costs for this more polar compound are likely responsible for the decreased affinity. In contrast, the 4-pyridones PT166 and PT159 have 3-4-fold enhanced affinities for saFabI with respect to the analogous 2-pyridones PT171 and PT420 (Table 1), consistent with a higher intrinsic potency of this scaffold. PT166 also potently inhibited ecFabI (Table 2), suggesting that the higher intrinsic potency may indeed translate to broad spectrum activity. Thus, substituting the methylene bridge of the initially reported 4-pyridones (Kitagawa et al. (2007). Bioorg. Med. Chem. 15:1106-16) with an ether linkage (Shin et al. (Feb. 3, 2011) Korea Patent WO/2011/014008 A2) seems to be a successful strategy to further improve FabI pyridone inhibitors.

Based on docking studies, herein suggested was a binding mode for the 4-pyridones similar to those observed for 2-pyridones (FIG. 6C). However, despite the enhanced affinity of PT166 with respect to PT171, the additional 4-methyl group is characterized by an unfavorable score. Thus, it was hypothesized that Phe-204 will change its conformational state upon 4-pyridone binding to avoid the steric interference with the N-methyl group. Because 4-pyridones did not co-crystallize with saFabI, PT155 was initially used, which carries an additional 4'-$NH_2$ group compared with PT166, and a ternary complex structure with *B. pseudomallei* FabI (bpFabI) was determined. Indeed, this structure confirmed the predicted 4-pyridone binding mode, and Phe-203 (corresponding to the saFabI residue Phe-204) was found to adopt a different conformation presenting one of its π-faces to the N-methyl group of PT155 (FIG. 6C). An ecFabI-NADH-PT166 structure (FIG. 6D) was solved, which further validated the proposed PT166-binding mode (FIG. 6C). Similar to the ecFabI-NADH-CG400549 structure, the substrate-binding loop was found to be disordered or in a very open conformation in these ecFabI and bpFabI structures, respectively. Interestingly, an open SBL conformation was very recently also observed in the structure of PT155 bound to InhA (Li et al. (2014) A structural and energetic model for the slow-onset inhibition of the *Mycobacterium tuberculosis* enoyl-ACP reductase InhA. ACS Chem. Biol. 9:986-93).

For the 4-pyridone analogues, in vitro MIC measurements against *S. aureus* RN4220 lie near the 2-pyridone linear correlation, consistent with their similar mode of action (FIG. 3B). To confirm that the main target of PT166 in vivo is indeed saFabI, selection experiments were performed, which resulted in mutations of the fabI gene in 4 of 5 sampled colonies, including the previously characterized A95V variant (Table 4) (Xu et al. (2008). Biochemistry 47:4228-36). Relative to CG400549, PT166 had a >50-fold lower MIC against an *E. coli* MG1655 strain lacking the efflux pump AcrAB, consistent with its more potent inhibition of ecFabI (Table 2). Relative to CG400549, PT166 also exhibited improved activity against the Gram-negative pathogens *F. tularensis* and *P. mirabilis* (Table 3). Thus, the spectrum of antibacterial activity by using ecFabI as the paradigm for Gram negative FabI homologues was extended. Furthermore, similar optimization principles were applicable for the inhibition of mycobacterial FabI proteins. PT166 bound more potently than CG400549 to the *M. tuberculosis* enoyl-ACP reductase InhA with $K_i$ values of 22 and 582 nM, respectively, and translated to significantly enhanced in vitro anti-mycobacterial activity (MIC=10.5 µM; Table 3).

Figure 8:
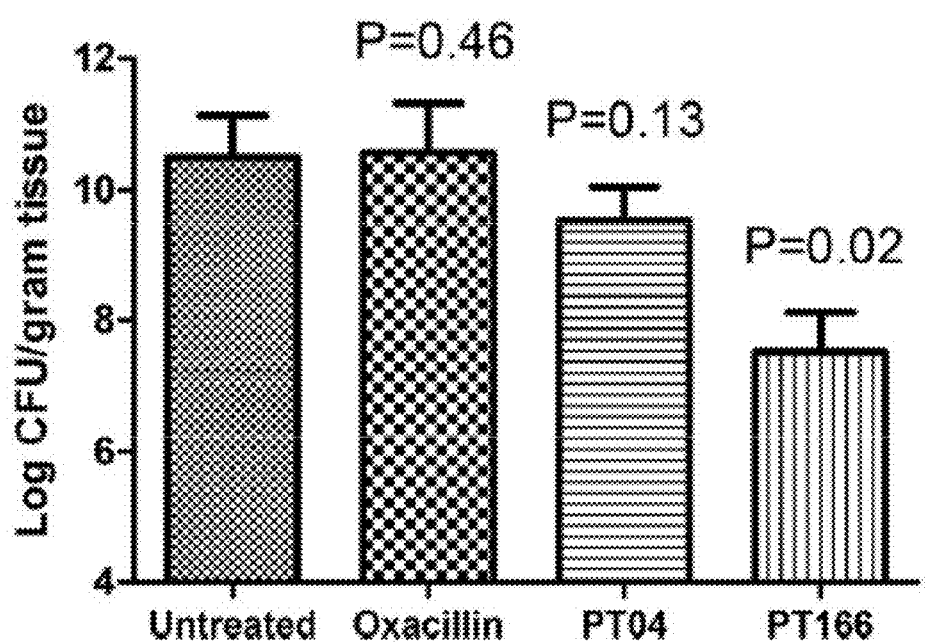
FIG. 8 is a graph showing the in vivo efficacy. The efficacy of selected compounds against MRSA strain BAA1762 in a neutropenic mouse thigh infection model is shown. Error bars represent the standard deviation for replicate data (n=5 in each group).

Pyridones are a metabolically stable alternative to diphenyl ethers, which contain a hydroxyl group that can be susceptible to glucuronidation and sulfonation (Wang et al. (2004). Drug. Metab. Dispos. 32:1162-9). This PK advantage may be key to the success of the clinical candidates CG400549 and AFN-1252. Importantly, PT166 maintained a superior PK profile compared with the diphenyl ether PT04 (Table 5). $C_{max}$ and $AUC_{0-24h}$ (where $AUC_{0-24h}$ is the area under the plasma concentration-time curve over 24 h) of PT166 are 9- and 5-fold higher than that of PT04, respectively, despite the fact that the dose of PT04 was double that of PT166. Also tested was the efficacy of PT166 in a neutropenic mouse model of MRSA infection. As a control, no bacteria were observed in the right thigh muscle of both treated and untreated mice, confirming the lack of significant migration of bacteria. In the infected thigh, however, significant bacterial burden was observed in the different treatment groups. As expected, oxacillin, a clinical antibiotic similar to methicillin, exhibited no in vivo antibacterial efficacy (FIG. 8). However, a 100 mg/kg intramuscular dose of PT166 significantly decreased the bacterial burden in the infected thigh by 2.8 log cfu/g tissue. In comparison, the same dose of the diphenyl ether PT04 only decreased the bacterial burden by 0.9 log cfu/g tissue.

Pyridones constitute a very promising and relatively new class of FabI inhibitors (Lu et al. (2008). Acc. Chem. Res. 41:11-20). Compared with diphenyl ethers, CG400549 has superior pharmacokinetic properties and proven clinical efficacy against *S. aureus* infections. However, it also has lower activity against many other important pathogens. Understanding the molecular basis for such selectivity can guide the development of pyridone-based FabI inhibitors with broad spectrum potential.

Despite the structural similarity of the pyridone and diphenyl ether scaffolds, there are differences with respect to their mode of inhibition, which have significant implications for the spectrum of activity. Pyridones bind predominantly to the E-NADPH complex, whereas diphenyl ethers exclusively interact with E-NADP$^+$ generated via catalysis (FIGS. 2, A and B). It was recently proposed that diphenyl ethers bind in a deprotonated state to their target. In such a scenario, the positively charged and thus electron-deficient oxidized nicotinamide ring of the cofactor forms a charge-assisted π-π stacking interaction with the electron-rich phenolate A-ring (FIG. 1). The inability of the much less acidic pyridones to form this ionic interaction might explain their reduced affinity for E-NADP$^+$.

Figure 9A:
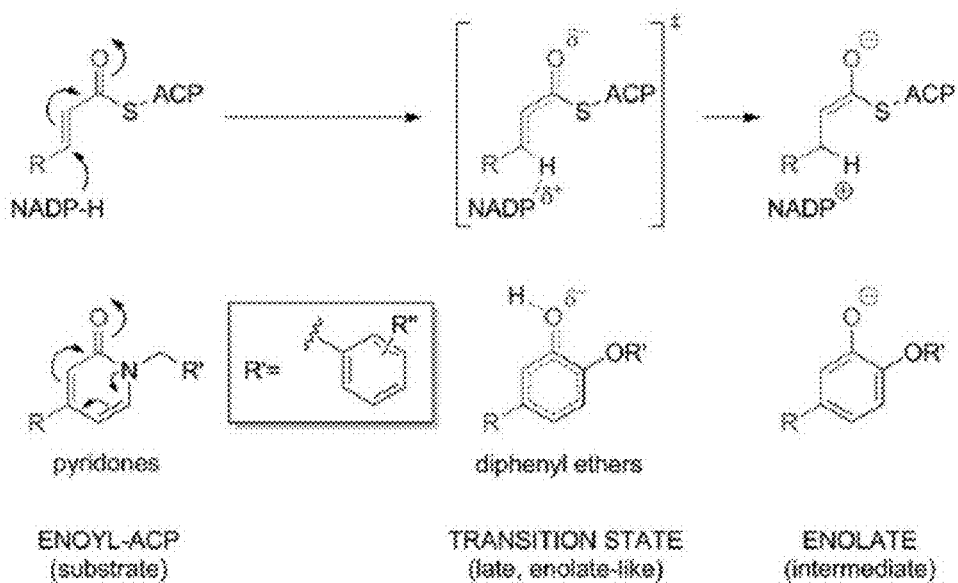
FIG. 9A is a depiction of conformational states sampled along the reaction coordinates of inhibitor binding and substrate turnover. Pyridone and diphenyl ether inhibitors resemble different species along the enzymatic reaction coordinate. In contrast to the enolate-like diphenyl ethers which are transition state analogues, pyridones are more substrate-like. The corresponding moieties of inhibitors and species along the reaction coordinate are highlighted.
Figure 9B:
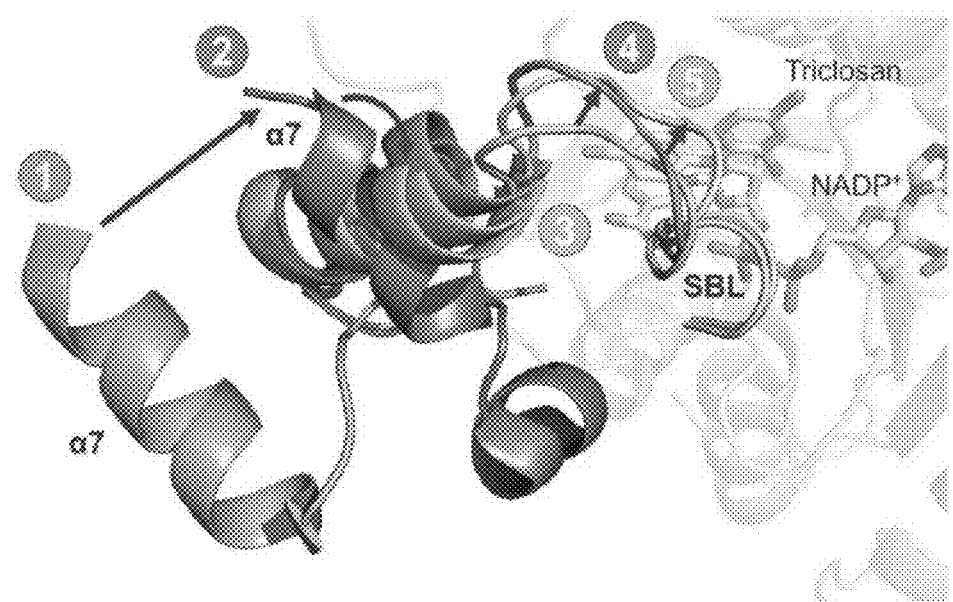
FIG. 9B. Conformational states sampled by the SBL and the attached helix α7 of saFabI. Arrows indicate the conformational changes proposed to occur during the enzymatic reaction (see also FIG. 9C). Prior to the binding of cofactor and substrate or inhibitor, the SBL is disordered, and helix α7 attains a very open conformation (state 1=PDB code 4ALM, subunit B; state 2=PDB code 4ALM, subunit C; further details about the conformational changes upon ligand binding are provided in a previous report (Schiebel et al. (2012) *Staphylococcus aureus* FabI: inhibition, substrate recognition, and potential implications for in vivo essentiality. Structure 20:802-3). The more substrate-like pyridone inhibitors likely induce a conformational state between the ternary E-NADPH-S complex and the transition state of the hydride transfer (state 3=CG400549-I structure, subunit C; state 4=CG400549-I structure, subunit A; see also FIG. 5B). In contrast, the transition state analogue triclosan and several other diphenyl ethers induce the likely fully closed state of the SBL (state 5=PDB code 4ALI, subunit H).
Figure 9C:
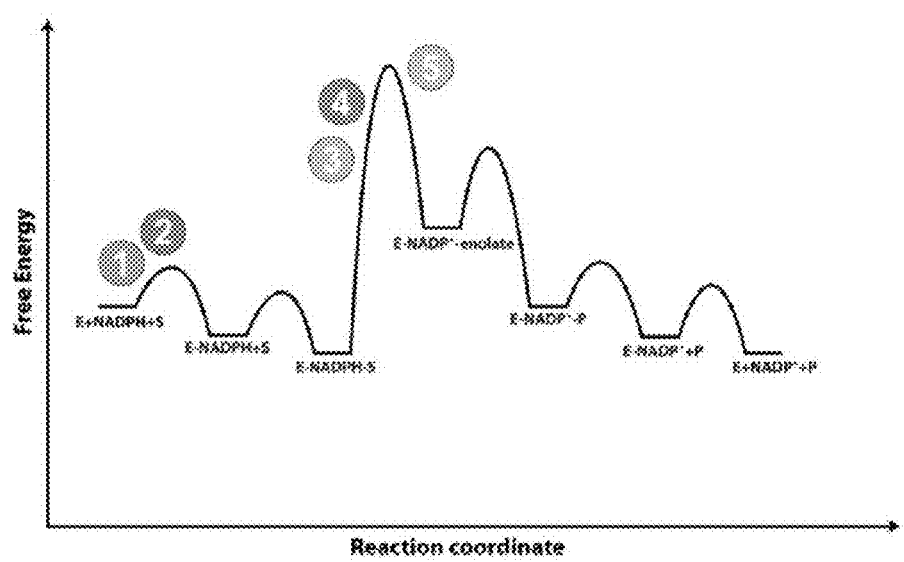
FIG. 9C. Qualitative energy diagram for substrate turnover by saFabI. The numbers 1-5 indicate the conformational states, which are likely sampled along the reaction coordinate of the enzymatic reaction (see also FIG. 9B).
Figure 9D:
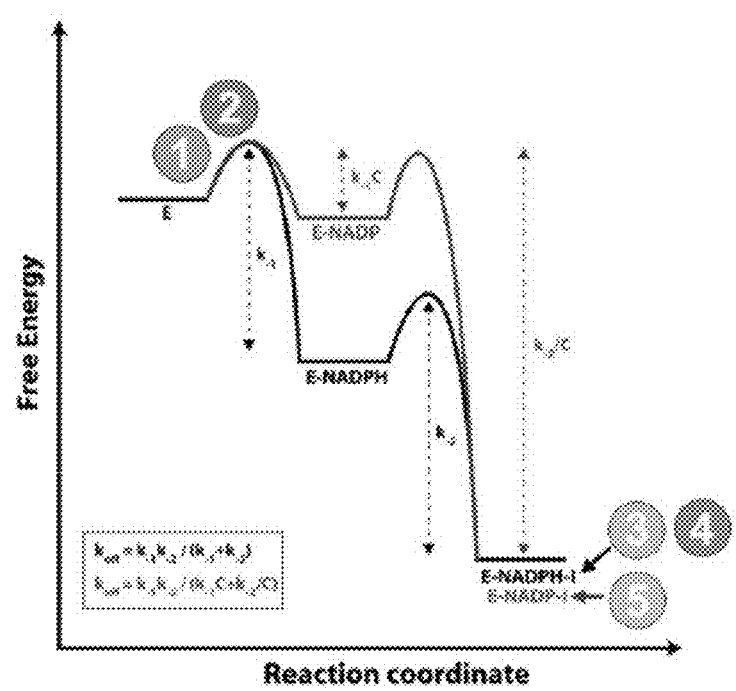
FIG. 9D. Approximate energy diagrams for saFabI in complex with NADPH and pyridone or NADP+ and diphenyl ether inhibitor. The overall affinities of both ternary complexes are assumed to be identical. By shifting stabilization from cofactor to inhibitor, the residence time of the overall complex is increased. This rationalizes the difference in off-rate kinetics between the diphenyl ethers and pyridones. Note that, technically, $k_{off}$ for the pyridone complex (E-NADPH-I) is equal to $k_{-2}$ because the E-NADPH complex is catalytically active. C is defined as a constant with a value greater than 1. The numbers 1-5 indicate the conformational states, which are likely sampled along the reaction coordinate of inhibitor binding (see also FIG. 9B).

The diphenyl ether and pyridone-bound saFabI ternary complexes likely reflect different stages during the hydride transfer step of the enzymatic reaction (FIG. 9A). It has recently been shown that diphenyl ethers are analogues of a late enolate-like transition state (Chang et al. (2013). Biochemistry 52:4217-22). In contrast, the pyridone structure more closely resembles the enoyl-ACP substrate (FIG. 9A) and thus binds preferably in a ternary complex with the reduced cofactor, which is present prior to the hydride transfer. It is envisioned that an incremental closure of the SBL during substrate binding and hydride transfer in which the loop is fully closed at the transition state to minimize its energy (FIG. 9). In this respect, the different conformations of the SBL presented herein define important structural snapshots along the reaction coordinate of enzyme catalysis (FIG. 5B). The observation of an opened substrate-binding site for pyridones confirms the hypothesis that these inhibitors are more substrate-like compared with the diphenyl ethers. In the light of the two alternatively ordered SBL conformations versus the disordered loop in the apoenzyme (FIG. 9B, states 1 and 2) (Schiebel et al. (2012). Structure 20:802-13; Priyadarshi et al. (2010). Proteins 78:480-6), it could be argued that the pyridone ternary complexes represent a state between the substrate complex and the transition state for enolate formation (FIG. 9C). The electron-donating effect of the pyridone nitrogen, which leads to a phenolate-like resonance structure, might thereby mimic the transfer of the negatively charged hydride ion (FIG. 9A).

As the hydride transfer reaction proceeds, the increasing positive charge on the nicotinamide ring and the closure of the substrate-binding loop shifts the balance of ternary complex stabilization more toward the fatty acyl relative to the cofactor component, which is reflected in the relative affinities of the investigated inhibitors and cofactor forms. The transition state mimicking diphenyl ethers display affinities that are 3 orders of magnitude higher compared with analogous substrate-like 2-pyridones, whereas NADP binds ~1000-fold less tightly to saFabI with respect to NADPH (FIG. 9D) (Chang et al. (2013). Biochemistry 52:4217-28). Accordingly, the cumulative ternary complex affinities ($K_i X K_{d,NADP(H)}$), which also integrate cofactor affinity, of comparable E-NADP$^+$-diphenyl ether and E-NADPH-pyridone complexes are calculated to be very similar. There is only a 2-fold difference in the cumulative affinity of the E-NADP$^+$-PT04 complex compared with the analogous E-NADPH-PT179 complex. Diphenyl ethers are stabilized to a greater extent partly because of the closure of the SBL that occurs farther along the reaction coordinate. At this stage, NADP$^+$ exists in the ternary complex, which also enhances the binding affinity of deprotonated diphenyl ethers. However, in comparison with E-NADPH, the steady-state concentration of E-NADP$^+$ is very small due to the fast dissociation of the oxidized cofactor generated via catalysis (Chang et al. (2013). Biochemistry 52:4217-28). Hence, the resulting apparent inhibitor association rate ($k_{on}$·[E-NADP$^+$]·[I]) of diphenyl ethers is slow explaining the observed slow binding phenomenon, although the actual association rate constants $k_{on}$ of pyridones and diphenyl ethers are very similar. Thus, in saFabI the ordering of the substrate-binding loop is likely correlated rather than causative with respect to the observation of slow-onset kinetics with diphenyl ethers. The slow-off kinetics observed with diphenyl ethers is likely the consequence of its potent thermodynamic affinity.

Among the three saFabI inhibitors investigated in clinical trials, CG400549 and AFN-1252 have been shown to be *Staphylococcus*-specific (Kaplan et al. (2012). Antimicrob. Agents Chemother. 56:5865-74; Silver, L. L. (2011) Challenges of antibacterial discovery. Clin. Microbiol. Rev. 24:71-109; Yum et al. (2007) In vitro activities of CG400549, a novel FabI inhibitor, against recently isolated clinical staphylococcal strains in Korea. Antimicrob. Agents Chemother. 51:2591-3; Park et al. (2007). J. Antimicrob. Chemother. 60:568-74), whereas the diphenyl ether MUT056399 is also active against several Gram-negative pathogens (Gerusz et al. (2012). J. Med. Chem. 55:9914-28). As depicted in FIG. 3, this is likely attributed to different modes of inhibition. Substrate accumulation weakens the intrinsic potency of competitive inhibitors in contrast to uncompetitive inhibitors. Thus, relatively unmodified diphenyl ethers are already able to potently inhibit cell growth. In contrast, further optimization of binding affinity is necessary for pyridones to achieve cellular efficacy, particularly in the presence of active efflux pumps. This argument likely extends to the naphthyridinones, such as AFN-1252, which was recently crystallized in complex with saFabI and 3'-NADPH (FIG. 1) (Kaplan et al. (2012). Antimicrob. Agents Chemother. 56:5865-74).

The structural data herein rationalize the pyridone SAR profile and clearly reveal the ability of the CG400549 5-, 2'-, and 3'-substituents to enhance its affinity toward saFabI (FIG. 4 and Table 1). In particular, the hydrogen bond formed between the CG400549 and PT173 3'-amino group with Ala-97 leads to a 6-fold increase in affinity (FIG. 4B). In the case of ecFabI, this hydrogen bond is not protected from solvent exposure due to an M99G substitution (FIG. 6B), thereby reducing the affinity of such compounds and increasing the selectivity of CG400549 for saFabI (Table 2). Because of the amino acid residues Ile-200 and Met-206 and an elongated C terminus, including Met-256', ecFabI also harbors a smaller binding pocket compared with saFabI (FIG. 6B). The wider acyl cavity of saFabI facilitates the accommodation of branched and longer acyl substrates or, analogously, bulky diphenyl ether 5-substituents (Schiebel et al. (2012). Structure 20:802-13; Chang et al. (2013). Biochemistry 52:4217-28; Sivaraman et al. (2003). Biochemistry 42:4406-13; Ward et al. (1999). Biochemistry 38:12514-25). Importantly, CG400549 and AFN-1252 contain large moieties at this position, which might further contribute to the *Staphylococcus*-specific spectrum of these two clinical trial inhibitors (FIG. 1). In fact, bulky pyridone 5-substituents interfere with the ecFabI and bpFabI SBL, although it is in a relatively closed state for saFabI with bound AFN-1252 (Kaplan et al. (2012). Antimicrob. Agents Chemother. 56:5865-74) and CG400549 (FIGS. 5B and 6A). This important difference might be further explained by the presence of the additional C-terminal extension in typical FabIs such as ecFabI and bpFabI, which occludes their substrate-binding sites (FIG. 7). In contrast, saFabI contains a significantly shorter C terminus compared with most other structurally characterized FabI proteins. The wider acyl cavity and thus the enhanced affinity of CG400549 can be related to the ability of saFabI to efficiently utilize bulky branched-chain fatty acyl substrates (Schiebel et al. (2012). Structure 20:802-813).

Based on the SAR profile of ecFabI, the ability to optimize binding affinity via substituents on the scaffold is very limited. A pyridone-based compound with broad spectrum activity must necessarily have higher intrinsic potency than the 2-pyridones. To achieve this, a 4-pyridone scaffold was used that retains the bridging oxygen of diphenyl ethers, thus providing an entropic advantage upon binding to FabI. Although the 4-pyridone inhibitor PT166 shares features with both the 2-pyridone and diphenyl ether scaffolds, its inhibition mechanism is the same as observed for 2-pyridones (FIG. 2B). Using the thermal shift assay, it was clearly shown that this compound inhibits saFabI at the E-NADPH stage (supplemental FIG. S2 of Schiebel et al., The Journal of Biological Chemistry, 2014, 289(23):15987-16005), just like CG400549 (FIG. 2A). The 2-pyridone/substrate-like behavior of PT166 is further confirmed by a comparison of the ecFabI structures. In contrast to the triclosan-bound structure (Stewart et al. (1999). J. Mol. Biol. 290:859-65), where the SBL is in a closed state, this loop is disordered in the complexes with PT166 and CG400549 (FIG. 6). Furthermore, the structure of InhA in complex with the 4-pyridone PT155 shares a very similar open SBL conformation with the substrate-bound form of this enzyme (Li et al. (2014). ACS Chem. Biol. 9:986-93; Rozwarski et al. (1999) Crystal structure of the *Mycobacterium tuberculosis* enoyl-ACP reductase, InhA, in complex with NAD and a C16 fatty acyl substrate. J. Biol. Chem. 274:15582-9). As expected based on these considerations, the SAR and predicted binding mode for the 4-pyridones is highly reminiscent of the 2-pyridone series, but 4-pyridones possess superior potency at the enzymatic and cellular levels (Tables 1 and 2). Importantly, the higher intrinsic potency also translates into an extended spectrum of activity for the promising lead compound PT166 (against *S. aureus, E. coli, F. tularensis, P. mirabilis,* and *M. tuberculosis*; Table 3). As with CG400549 (Ro et al. (2009) Interscience Conference on Antimicrobial Agents and Chemotherapy, San Francisco, Calif., Sep. 12-15, 2009, American Society for Microbiology, San Francisco), replacement of the metabolically labile hydroxyl group with a carbonyl successfully improved the pharmacokinetic profile of PT166 compared with the diphenyl ether PT04 (Table 5). Additionally, this compound primarily acts on target (Table 4), and it significantly reduced bacterial burden in a murine model of MRSA infection (FIG. 8), validating its potential as a drug lead for future optimization and development. Further in vivo studies are needed to more precisely compare the pharmacokinetics and efficacy of the diverse FabI inhibitor scaffolds.

Thus, the structural and mechanistic basis for selective saFabI inhibition by pyridones, including the clinical candidate CG400549, has been elucidated. A rational design of the lead compound PT166, which merges the pharmacokinetic advantages of a pyridone with the potential for an extended spectrum of antibacterial activity, has been provided. ecFabI and InhA served as paradigms for enoyl-ACP reductase homologues in Gram-negative and mycobacterial organisms, respectively. A similar approach can be applied toward the development of much needed narrow and broad spectrum antibiotics against novel targets.

Marrakchi et al. (2000) InhA, a target of the antituberculous drug isoniazid, is involved in a mycobacterial fatty acid elongation system, FAS-II. Microbiology 146:289-96; Zhang et al. (2006) Inhibiting bacterial fatty acid synthesis. J. Biol. Chem. 281:17541-4; Payne et al. (2002) Discovery of a novel and potent class of FabI-directed antibacterial agents. Antimicrob. Agents Chemother. 46:3118-24; Banerjee et al. (1994) inhA, a gene encoding a target for isoniazid and ethionamide in *Mycobacterium tuberculosis*. Science 263:227-30; Dessen et al. (1995) Crystal structure and function of the isoniazid target of *Mycobacterium tuberculosis*. Science 267:1638-41; Levy et al. (1999) Molecular basis of triclosan activity. Nature 398:383-4; Heath et al. (1999) Mechanism of triclosan inhibition of bacterial fatty acid synthesis. J. Biol. Chem. 274:11110-4; Payne et al. (2007) Drugs for bad bugs: confronting the challenges of antibacterial discovery. Nat. Rev. Drug. Discov. 6:29-40; Heath et al. (2000) Atriclosan-resistant bacterial enzyme. Nature 406:145-6; Heath et al. (2000) The enoyl-[acyl-carrier-protein] reductases FabI and FabL from *Bacillus subtilis*. J. Biol. Chem. 275:40128-33: Massengo-Tiassé et al. (2008) *Vibrio cholerae* FabV defines a new class of enoyl-acyl carrier protein reductase. J. Biol. Chem. 283: 1308-16; Brinster et al. (2009) Type II fatty acid synthesis is not a suitable antibiotic target for Gram-positive pathogens. Nature 458:83-6; Parsons et al. (2011) Metabolic basis for the differential susceptibility of Gram-positive pathogens to fatty acid synthesis inhibitors. Proc. Natl. Acad. Sci. U.S.A. 108:15378-83; Balemans et al. (2010) Essentiality of FASII pathway for *Staphylococcus aureus*. Nature 463:E3; Seefeld et al. (2003) Indole naphthyridinones as inhibitors of bacterial enoyl-ACP reductases FabI and FabK. J. Med. Chem. 46:1627-35; Emsley et al. (2004) Coot: model-building tools for molecular graphics. Acta Crystallogr. D Biol. Crystallogr. 60:2126-32.

TABLE 1

Thermodynamic parameters for inhibitors of saFabI[a]

| Name | Structure | $K_i^{app}$ (nM) [b] | $K_i$ (nM) | MIC (µM) [c] |
|---|---|---|---|---|
| CG400549 | 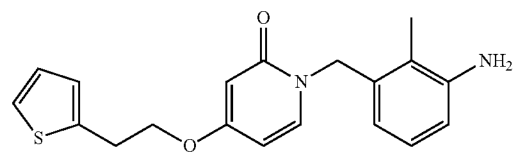 [SMILES: Cc1c(N)cccc1Cn1ccc(OCCc2cccs2)cc1=O] | 4.7 ± 0.9 | 1.3 ± 0.1 | 5.9 |
| PT173 | 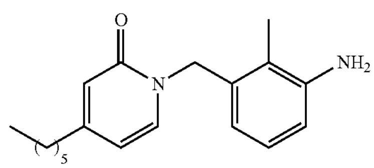 | 7.3 ± 1.5 | 2.0 ± 0.4 | 6.7 |
| PT171 | 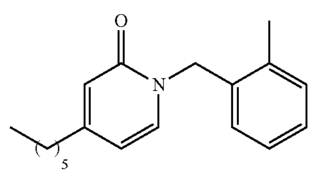 | 44.3 ± 6.6 | 11.9 ± 1.8 | n.d. [d] |
| PT179 | 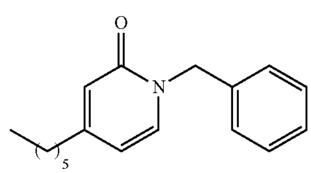 | 70.4 ± 9.8 | 19.0 ± 2.7 | 118.8 |
| PT420 | 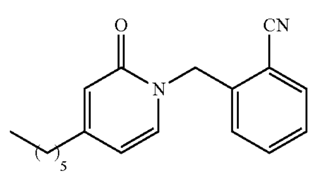 | 109.8 ± 1.7 | 29.6 ± 9.5 | 108.7 |
| PT172 | 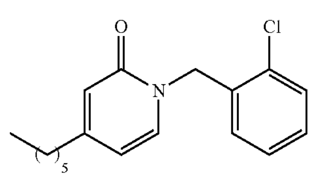 | 40.7 ± 1.3 | 11.0 ± 0.4 | 26.3 |

TABLE 1-continued

Thermodynamic parameters for inhibitors of saFabI[a]

| Name | Structure | $K_i^{app}$ (nM) [b] | $K_i$ (nM) | MIC (μM) [c] |
|---|---|---|---|---|
| PT170 | 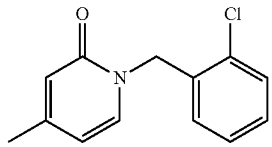 [SMILES: Cc1ccn(Cc2ccccc2Cl)c(=O)c1] | 848.6 ± 19.3 | 228.7 ± 5.2 | >500 |
| PT166 | 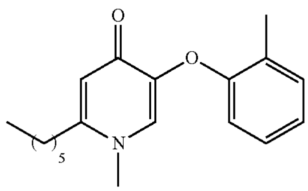 | 10.1 ± 2.1 | 2.7 ± 0.6 | 0.8 |
| PT159 | 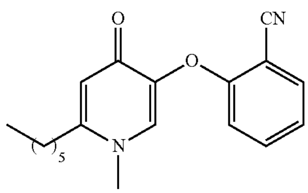 | 41.0 ± 3.4 | 11.0 ± 0.9 | 12.9 |
| PT191 | 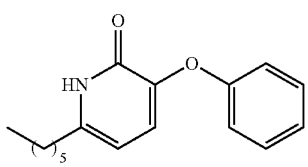 | 729.3 ± 82.4 | 196.5 ± 22.2 | n.d. [d] |
| PT01 [e] | 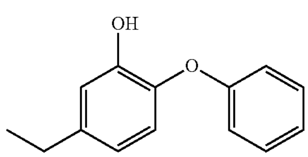 [SMILES: CCc1ccc(Oc2ccccc2)c(O)c1] | 120.8 ± 10.1 | 0.09 ± 0.01 | 2.3 |
| PT51 [e] | 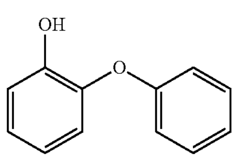 [SMILES: Oc1ccccc1Oc1ccccc1] | 24515.0 ± 1359.8 | 18.9 ± 1.1 | 687.4 |
| PT53 [e] | 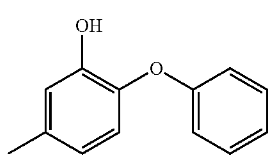 | 493.7 ± 40.2 | 0.38 ± 0.03 | 20.0 |

[a] Curve fitting errors are reported for each value in the table.
[b] $[S]/K_S = 2$
[c] Value was reported against *S. aureus* RN4220.
[d] n.d. means not determined.
[e] Binds to the E-NADP+ binary complex: $K_i$ and $K_i^{app}$ values were obtained from Ref 31.

TABLE 2

Thermodynamic parameters for inhibitors of ecFabI[a]

| Name | Structure | $K_i^{app}$ (nM) [b] | $K_i$ (nM) | MIC (μM) [c] |
|---|---|---|---|---|
| CG400549 | 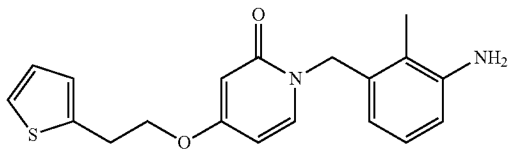 [SMILES: Cc1c(N)cccc1Cn1ccc(OCCc2cccs2)cc1=O] | 99.4 ± 2.3 | 81.9 ± 1.9 | >375 |
| PT173 | 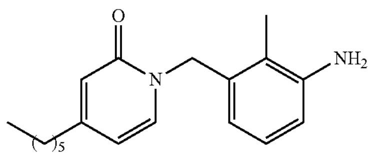 | 246.0 ± 10.1 | 202.6 ± 8.3 | >425 |
| PT171 | 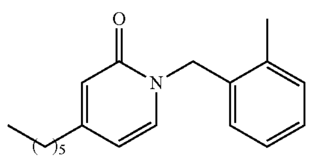 | 116.2 ± 4.6 | 95.7 ± 3.8 | n.d. [d] |
| PT166 | 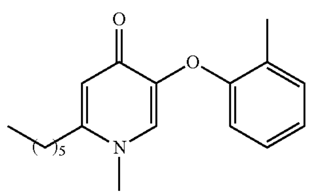 | 8.5 ± 0.2 | 7.0 ± 0.1 | 6.7 [e] |
| PT01 [f] | 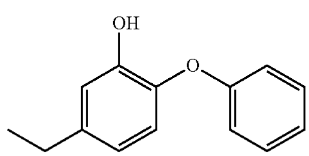 [SMILES: CCc1ccc(Oc2ccccc2)c(O)c1] | 33.6 | 0.2 | 0.6 [g] |
| PT04 [f] | 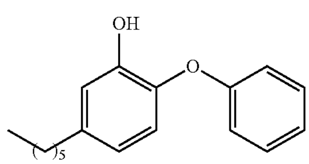 | 32.2 | 0.2 | 14.8 [g] |
| PT52 [f] | 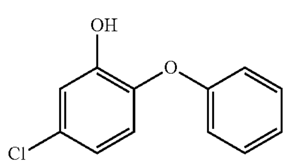 [SMILES: Oc1cc(Cl)ccc1Oc1ccccc1] | 26.9 | 0.1 | 0.1 [g] |
| PT55 [f] | 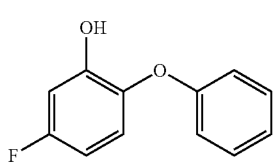 [SMILES: Oc1cc(F)ccc1Oc1ccccc1] | 92.6 | 1.1 | 1.2 [g] |

[a] Curve fitting errors are reported for each value in the table.
[b] [S]/$K_S$ = 0.19.
[c] Value is reported against *E. coli* MG1655 ΔacrAB, a strain with a knockout of the specific efflux pump AcrAB.
[d] n.d. means not determined.
[e] The MIC value against *E. coli* MG1655 with the intact AcrAB efflux pump is >425 μm.
[f] This binds to the E-NAD[+] binary complex. $K_i$ and $K_i^{app}$ values were determined via single point progress curve analysis, as described in Ref. 31. Rationally derived kinetic parameters for each step in the mechanistic model depicted in FIG. 2B are listed in supplemental Table S3.
[g] MIC values against *E. coli* MG1655 with the intact AcrAB efflux pump were 10-30-fold higher.

TABLE 3

Spectrum of antibacterial activity for different classes of FabI inhibitors

| Organism | Enoyl-reductase isoform[a] | MIC (μm) PT01 | MIC (μm) CG400549 | MIC (μm) PT166 |
|---|---|---|---|---|
| S. aureus RN4220 | FabI | 2.3 | 5.9 | 0.8 |
| E. coli MG1655 | FabI | 18.7 | >375 | >425 |
| E. coli MG1655 ΔacrAB[b] | FabI | 0.6 | >375 | 6.7 |
| F. tularensis LVS | FabI | 0.1[c] | 5.9 | 0.4 |
| P. mirabilis ATCC35659 | FabI | ND[d] | >750 | 213.8 |
| M. tuberculosis H37Rv | FabI | 72.9 | >300 | 10.5 |
| B. pseudomallei Bp400[b] | FabI and FabV | 326.7[e] | 376.0 | 213.8 |

[a]Data are according to Refs. 23, 24, 29, 81.
[b]Strains with knock-out of specific efflux pumps are shown.
[c]Data are according to Ref. 69.
[d]ND means not determined.
[e]Data are according to Ref. 35.

TABLE 4

Selection S. aureus RN4220 resistance to PT166

| Strain | Nucleotide change | Amino acid change | MIC μm |
|---|---|---|---|
| RN4220 | | | 0.8 |
| 166R.1 | GCA → GTA | A95V | 8.8 |
| 166R.2 | GCA → GTA | A95V | 8.8 |
| 166R.3 | GCA → GTA TTC → TTG | A95V F252L | 8.8 |
| 166R.4 | GCA → GTA GAA → GAT | A95V E71D | 8.8 |
| 166R.5 | No change | No change | 17.6 |

TABLE 5

In vivo pharmacokinetic profile for PT166 and PT04

| PK parameter | PT04 | PT166 |
|---|---|---|
| Dosage (mg/kg) | 200 | 100 |
| $AUC_{0-24}$ (μg h/ml)[a] | 11.8 | 53.0 |
| $t_{1/2}$ (h)[b] | 4.5 | 2.7 |
| $t_{max}$ (h)[c] | 1.0 | 0.25 |
| $C_{max}$ (μg/ml)[d] | 5.1 | 45.9 |

[a]$AUC_{0-24}$ is the area under the plasma concentration-time curve over 24 h.
[b]$t_{1/2}$ is the time taken for plasma concentration to fall to 50% of its original value.
[c]$t_{max}$ is the time when $C_{max}$ occurs.
[d]$C_{max}$ in the maximum plasma concentration of the drug.

FabI Inhibition and MIC Data for 2-Pyridones

| Compound | MW | clogP | $K_i$ (nM) | Escherichia coli MIC (μg/mL) MG1655 ΔacrAB | Staphylococcus aureus IC$_{50}$ (nM) [E] = 50 nM | Staphylococcus aureus MIC (μg/mL) RN4220 | Mycobacterium tuberculosis IC$_{50}$ (nM) [E] = 100 nM | Mycobacterium tuberculosis MIC (μg/mL) H37Rv | Francisella tularensis IC$_{50}$ (nM) [E] = 100 nM | Francisella tularensis MIC (μg/mL) LVS | Burkholderia pseudomallei IC$_{50}$ (nM) [E] = 30 nM | Burkholderia pseudomallei MIC (μg/mL) Bt38 | Yersinia pestis YpFabV $K_i$ (μM) |
|---|---|---|---|---|---|---|---|---|---|---|---|---|---|
| PT170 | 233.69 | 2.89 | | | >1000 ($K_i$ 228.7 ± 5.2 nM) | >500 | >1700 | >50 | 202 ± 17 | 49.98 | >1000 | ND | |
| PT171 | 283.41 | 5.27 | 95.7 ± 3.8 | nd | 150 ± 22 ($K_i$ 11.9 ± 1.8 nM) | 5 | 130 ± 21 [E] = 50 nM | 25 | 83 ± 32 | 3.65 | ~400 | 153.7 | |
| PT172 | 303.83 | 5.54 | | | 379 ± 88 ($K_i$ 11.0 ± 0.4 nM) | 5, 8 | 240 ± 44 | 25 | 61 ± 13 | 4.04 | 260 ± 9.3 | 250 | |
| PT173 | 298.42 | 4.00 | 202.6 ± 8.3 | >425 | 68 ± 14 ($K_i$ 2.0 ± 0.4 nM) | 2, 5 | >3200 | 50 | 83 ± 15 | 3.57 | 460 ± 10 | 36.3 | |
| PT174 | 328.41 | 4.94 | | | 248 ± 20 | 50 | | | 85 ± 11 | 2.123 | ND | 250 | |
| PT175 | 288.36 | 3.56 | | | >1000 | 50 | >4000 | 50 | ND | 13.97 | >1000 | 78.32 | |
| PT179 | 269.38 | 4.83 | | | 192 ± 30 ($K_i$ 19.0 ± 2.7 nM) | 32 | | | | | | | |
| PT191 | 271.35 | 4.67 | | | >2000 ($K_i$ 196.5 ± 22.2 nM) | No inhibition | 10% inhibition [I] = 2 μM [E] = 100 nM | ND | >10000 | ND | >3000 | ND | |
| PT192 | 285.38 | 5.17 | | | ND | No inhibition | | | ND | 9.2 | ND | 8.35 | |

| FabI Inhibition and MIC Data for 2-Pyridones | | | | | | | | | | | | |
|---|---|---|---|---|---|---|---|---|---|---|---|---|
| | | | | *Escherichia coli* | *Staphylococcus aureus* | | *Mycobacterium tuberculosis* | | *Francisella tularensis* | | *Burkholderia pseudomallei* | |
| Compound | MW | clogP | $K_i$ (nM) | MIC (μg/mL) MG1655 ΔacrAB | $IC_{50}$ (nM) [E] = 50 nM | MIC (μg/mL) RN4220 | $IC_{50}$ (nM) [E] = 100 nM | MIC (μg/mL) H37Rv | $IC_{50}$ (nM) [E] = 100 nM | MIC (μg/mL) LVS | $IC_{50}$ (nM) [E] = 30 nM | MIC (μg/mL) Bt38 | *Yersinia pestis* YpFabV $K_i$ (μM) |
| PT420 | 294.39 | 4.40 | | | 746 ± 165 ($K_i$, 29.6 ± 0.5 nM) | 32 | | | 727 ± 84 | 10.214 | ND | 44.4 | |
| PT421 | 287.37 | 4.97 | | | 297 ± 64 | 2 | | | | | | | |
| PT422 | 287.37 | 4.97 | | | 222 ± 22 | 1 | | | | | | | |
| PT423 | 287.37 | 4.97 | | | 165 ± 22 | 16 | | | | | | | |
| PT424 | 314.38 | 4.57 | | | 1500 ± 200 | ND | | | | | | | 11 |
| PT425 | 284.4 | 3.60 | | | 380 ± 20 | ~32 | | | | | | | |
| PT426 | 303.83 | 5.54 | | | 185 ± 18 | ~32 | | | | | | | |
| PT427 | 311.42 | 4.27 | | | 394 ± 40 | >128 | | | | | | | |

| FabI Inhibition and MIC Data for 4-Pyridones | | | | | | | | | | | | | |
|---|---|---|---|---|---|---|---|---|---|---|---|---|---|
| | | | *Escherichia coli* | | *Staphylococcus aureus* | | *Mycobacterium tuberculosis* | | *Francisella tularensis* | | *Burkholderia pseudomallei* $IC_{50}$ (μM) | | *Yersinia pestis* YpFabV $IC_{50}$ |
| Compound | MW | clogP | $K_i$ (nM) | MIC (μg/mL) MG1655 ΔacrAB | $K_i$ (nM) | MIC (μg/mL) RN4220 | $IC_{50}$ (nM) [E] = 50 nM | MIC (μg/mL) H37Rv | $IC_{50}$ (μM) [E] = 100 nM | MIC (μg/mL) LVS | 7.5 nM FabV 30 nM FabI | MIC (μg/mL) Bt38 | (μM) [E] = 15 nM | MIC (μg/mL) |
| PT151 | 294.69 | 1.15 | | | | | No inhibition at 1 μM | NA | | | | | | |
| PT152 | 308.72 | 1.65 | | | | | 2252 ± 148 | 12.5 | | | | | | |
| PT155 | 314.42 | 3.26 | | | | | 107 ± 16 | 6.25 | 0.053 ± 0.014 | 91% inhib. @ 5 μg/ml | 3 ± 0.6 (bpFabV) 0.14 ± 0.02 (bpFabI) | 90% inhib. @ 20 μg/ml | >50 | 26% inhib. @ 40 μg/ml |
| PT156 | 330.38 | 3.73 | | | | | 407 ± 37 | 50 | | 88% inhib. @ 5 μg/ml | 0.56 ± 0.1 (bpFabV) 0.96 ± 0.1 (bpFabI) | 43% inhib. @ 40 μg/ml | 0.18 ± 0.04 | 29% inhib. @ 40 μg/ml |
| PT157 | 300.4 | 2.76 | | | | | 424 ± 132 | 50 | | | 1 ± 0.3 (bpFabV) 0.87 ± 0.9 (bpFabV) | | 0.13 ± 0.03 | |
| PT159 | 310.39 | 3.42 | | | 11.0 ± 0.9 nM | 4 | 629 ± 19 | 50 | | | | | | |
| PT165 | 344.4 | 4.23 | | | | | | | | | | | | |
| PT166[a] | 299.41 | 4.48 | 7.0 ± 0.1 | 2 (MIC > 128 for MG1655 with intact efflux pump) | 2.7 ± 0.6 | 0.24 | 28.6 ± 4.7 | 3.13 | 0.024 ± 0.004 | 0.12, 0.85 | | 64 Bp400 | | |
| PT167 | 311.38 | 2.32 | | | | | 979 ± 152 | 100 | | | | | | |
| PT168 | 286.37 | 2.49 | | | | | 1778 ± 315 | 50 | | | | | | |
| PT169 | 301.38 | 2.34 | | | | | 379 ± 41 | 12.5 | | | | | | |
| PT190 | 304.36 | 2.52 | | | | | 641 ± 55 | 25 | | | | | | |

INCORPORATION OF SEQUENCE LISTING

Incorporated herein by reference in its entirety is the Sequence Listing for the application. The Sequence Listing is disclosed on a computer-readable ASCII text file titled, "178-433_Sequence_Listing.txt", created on Jul. 5, 2016. The "sequence.txt" file is 28 kb in size.

The invention claimed is:
1. A 4-pyridone compound having the formula:
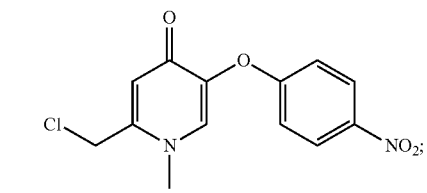
PT151
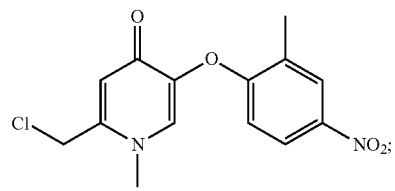
PT152
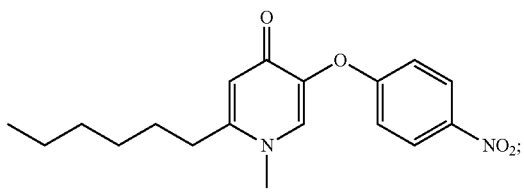
PT156
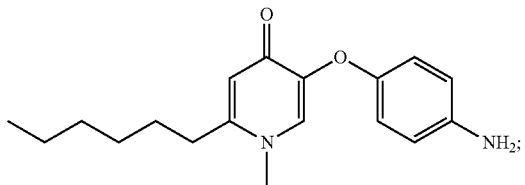
PT157
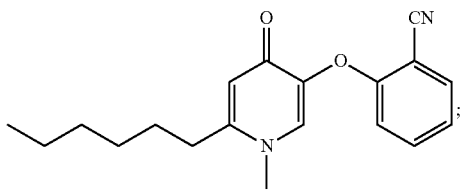
PT159
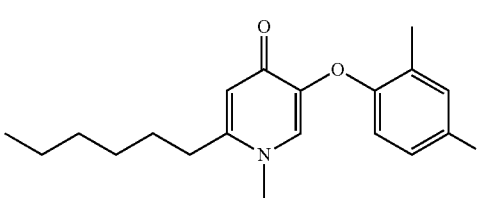
PT165
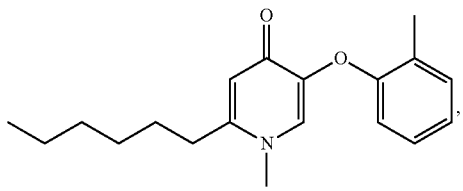
PT166
or a pharmaceutically acceptable salt thereof.
* * * * *

```
                          SEQUENCE LISTING

<160> NUMBER OF SEQ ID NOS: 12

<210> SEQ ID NO 1
<211> LENGTH: 256
<212> TYPE: PRT
<213> ORGANISM: Staphylococcus aureus

<400> SEQUENCE: 1

Met Leu Asn Leu Glu Asn Lys Thr Tyr Val Ile Met Gly Ile Ala Asn
1               5                   10                  15

Lys Arg Ser Ile Ala Phe Gly Val Ala Lys Val Leu Asp Gln Leu Gly
            20                  25                  30

Ala Lys Leu Val Phe Thr Tyr Arg Lys Glu Arg Ser Arg Lys Glu Leu
        35                  40                  45

Glu Lys Leu Leu Glu Gln Leu Asn Gln Pro Glu Ala His Leu Tyr Gln
    50                  55                  60

Ile Asp Val Gln Ser Asp Glu Glu Val Ile Asn Gly Phe Glu Gln Ile
65                  70                  75                  80

Gly Lys Asp Val Gly Asn Ile Asp Gly Val Tyr His Ser Ile Ala Phe
                85                  90                  95

Ala Asn Met Glu Asp Leu Arg Gly Arg Phe Ser Glu Thr Ser Arg Glu
            100                 105                 110

Gly Phe Leu Leu Ala Gln Asp Ile Ser Ser Tyr Ser Leu Thr Ile Val
        115                 120                 125

Ala His Glu Ala Lys Lys Leu Met Pro Glu Gly Gly Ser Ile Val Ala
    130                 135                 140

Thr Thr Tyr Leu Gly Gly Glu Phe Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175

Asp Leu Gly Pro Asp Asn Ile Arg Val Asn Ala Ile Ser Ala Gly Pro
            180                 185                 190

Ile Arg Thr Leu Ser Ala Lys Gly Val Gly Gly Phe Asn Thr Ile Leu
        195                 200                 205

Lys Glu Ile Glu Glu Arg Ala Pro Leu Lys Arg Asn Val Asp Gln Val
    210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Ser Gly Phe His Ala Ile Lys
                245                 250                 255

<210> SEQ ID NO 2
<211> LENGTH: 256
<212> TYPE: PRT
<213> ORGANISM: Staphylococcus epidermidis

<400> SEQUENCE: 2

Met Leu Asn Leu Glu Asn Lys Thr Tyr Val Ile Met Gly Ile Ala Asn
1               5                   10                  15

Lys Arg Ser Ile Ala Phe Gly Val Ala Lys Val Leu Asp Arg Leu Gly
            20                  25                  30

Ala Lys Leu Val Phe Thr Tyr Arg Lys Glu Arg Ser Arg Lys Glu Leu
```

```
              35                  40                  45
Glu Lys Leu Leu Glu Gln Leu Asn Gln Ser Glu His His Leu Tyr Glu
 50                  55                  60

Ile Asp Val Gln Asn Asp Glu Asp Ile Ile Asn Gly Phe Ser Gln Ile
 65                  70                  75                  80

Gly Lys Asp Val Gly Gln Ile Asp Gly Val Tyr His Ser Ile Ala Phe
                 85                  90                  95

Ala Asn Met Glu Asp Leu Arg Gly Arg Phe Ser Glu Thr Ser Arg Glu
            100                 105                 110

Gly Phe Leu Leu Ala Gln Glu Ile Ser Ser Tyr Ser Leu Thr Leu Val
        115                 120                 125

Ala His Glu Ala Lys Lys Leu Met Pro Glu Gly Gly Ser Ile Val Ala
    130                 135                 140

Thr Thr Tyr Ile Gly Gly Glu Ala Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175

Asp Leu Gly Glu Asp Asn Ile Arg Val Asn Ala Ile Ser Ala Gly Pro
            180                 185                 190

Ile Arg Thr Leu Ser Ala Lys Gly Val Gly Gly Phe Asn Thr Ile Leu
        195                 200                 205

Lys Glu Ile Glu Ala Arg Ala Pro Leu Lys Arg Asn Val Asp Gln Glu
    210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Gly Gly Phe His Ala Ile Lys
                245                 250                 255

<210> SEQ ID NO 3
<211> LENGTH: 262
<212> TYPE: PRT
<213> ORGANISM: Escherichia coli

<400> SEQUENCE: 3

Met Gly Phe Leu Ser Gly Lys Arg Ile Leu Val Thr Gly Val Ala Ser
  1               5                  10                  15

Lys Leu Ser Ile Ala Tyr Gly Ile Ala Gln Ala Met His Arg Glu Gly
                 20                  25                  30

Ala Glu Leu Ala Phe Thr Tyr Gln Asn Asp Lys Leu Lys Gly Arg Val
             35                  40                  45

Glu Glu Phe Ala Ala Gln Leu Gly Ser Asp Ile Val Leu Gln Cys Asp
 50                  55                  60

Val Ala Glu Asp Ala Ser Ile Asp Thr Met Phe Ala Glu Leu Gly Lys
 65                  70                  75                  80

Val Trp Pro Lys Phe Asp Gly Phe Val His Ser Ile Gly Phe Ala Pro
                 85                  90                  95

Gly Asp Gln Leu Asp Gly Asp Tyr Val Asn Ala Val Thr Arg Glu Gly
            100                 105                 110

Phe Lys Ile Ala His Asp Ile Ser Ser Tyr Ser Phe Val Ala Met Ala
        115                 120                 125

Lys Ala Cys Arg Ser Met Leu Asn Pro Gly Ser Ala Leu Leu Thr Leu
    130                 135                 140

Ser Tyr Leu Gly Ala Glu Arg Ala Ile Pro Asn Tyr Asn Val Met Gly
145                 150                 155                 160
```

```
Leu Ala Lys Ala Ser Leu Glu Ala Asn Val Arg Tyr Met Ala Asn Ala
            165                 170                 175

Met Gly Pro Glu Gly Val Arg Val Asn Ala Ile Ser Ala Gly Pro Ile
        180                 185                 190

Arg Thr Leu Ala Ala Ser Gly Ile Lys Asp Phe Arg Lys Met Leu Ala
    195                 200                 205

His Cys Glu Ala Val Thr Pro Ile Arg Arg Thr Val Thr Ile Glu Asp
210                 215                 220

Val Gly Asn Ser Ala Ala Phe Leu Cys Ser Asp Leu Ser Ala Gly Ile
225                 230                 235                 240

Ser Gly Glu Val Val His Val Asp Gly Phe Ser Ile Ala Ala Met
                245                 250                 255

Asn Glu Leu Glu Leu Lys
            260
```

<210> SEQ ID NO 4
<211> LENGTH: 263
<212> TYPE: PRT
<213> ORGANISM: Burkholderia pseudomallei

<400> SEQUENCE: 4

```
Met Gly Phe Leu Asp Gly Lys Arg Ile Leu Thr Gly Leu Leu Ser
1               5                   10                  15

Asn Arg Ser Ile Ala Tyr Gly Ile Ala Lys Ala Cys Lys Arg Glu Gly
            20                  25                  30

Ala Glu Leu Ala Phe Thr Tyr Val Gly Asp Arg Phe Lys Asp Arg Ile
        35                  40                  45

Thr Glu Phe Ala Ala Glu Phe Gly Ser Glu Leu Val Phe Pro Cys Asp
    50                  55                  60

Val Ala Asp Asp Ala Gln Ile Asp Ala Leu Phe Ala Ser Leu Lys Thr
65                  70                  75                  80

His Trp Asp Ser Leu Asp Gly Leu Val His Ser Ile Gly Phe Ala Pro
                85                  90                  95

Arg Glu Ala Ile Ala Gly Asp Phe Leu Asp Gly Leu Thr Arg Glu Asn
            100                 105                 110

Phe Arg Ile Ala His Asp Ile Ser Ala Tyr Ser Phe Pro Ala Leu Ala
        115                 120                 125

Lys Ala Ala Leu Pro Met Leu Ser Asp Asp Ala Ser Leu Leu Thr Leu
    130                 135                 140

Ser Tyr Leu Gly Ala Glu Arg Ala Ile Pro Asn Tyr Asn Thr Met Gly
145                 150                 155                 160

Leu Ala Lys Ala Ala Leu Glu Ala Ser Val Arg Tyr Leu Ala Val Ser
                165                 170                 175

Leu Gly Ala Lys Gly Val Arg Val Asn Ala Ile Ser Ala Gly Pro Ile
            180                 185                 190

Lys Thr Leu Ala Ala Ser Gly Ile Lys Ser Phe Gly Lys Ile Leu Asp
        195                 200                 205

Phe Val Glu Ser Asn Ser Pro Leu Lys Arg Asn Val Thr Ile Glu Gln
    210                 215                 220

Val Gly Asn Ala Gly Ala Phe Leu Leu Ser Asp Leu Ala Ser Gly Val
225                 230                 235                 240

Thr Ala Glu Val Met His Val Asp Ser Gly Phe Asn Ala Val Val Gly
                245                 250                 255

Gly Met Ala Gly Leu Glu Glu
            260
```

<210> SEQ ID NO 5
<211> LENGTH: 260
<212> TYPE: PRT
<213> ORGANISM: Francisella tularensis

<400> SEQUENCE: 5

Met Gly Phe Ala Leu Gly Lys Lys Ile Leu Ile Thr Gly Leu Leu Ser
1               5                   10                  15

Asn Lys Ser Ile Ala Tyr Gly Ile Ala Lys Ala Met His Arg Glu Gly
            20                  25                  30

Ala Glu Leu Ala Phe Thr Tyr Val Gly Gln Phe Lys Asp Arg Val Glu
        35                  40                  45

Lys Leu Cys Ala Glu Phe Asn Pro Ala Ala Val Leu Pro Cys Asp Val
    50                  55                  60

Ile Ser Asp Gln Glu Ile Lys Asp Leu Phe Val Glu Leu Gly Lys Val
65                  70                  75                  80

Trp Asp Gly Leu Asp Ala Ile Val His Ser Ile Ala Phe Ala Pro Arg
                85                  90                  95

Asp Gln Leu Glu Gly Asn Phe Ile Asp Cys Val Thr Arg Glu Gly Phe
            100                 105                 110

Ser Ile Ala His Asp Ile Ser Ala Tyr Ser Phe Ala Ala Leu Ala Lys
        115                 120                 125

Glu Gly Arg Ser Met Met Lys Asn Arg Asn Ala Ser Met Val Ala Leu
    130                 135                 140

Thr Tyr Ile Gly Ala Glu Lys Ala Met Pro Ser Tyr Asn Thr Met Gly
145                 150                 155                 160

Val Ala Lys Ala Ser Leu Glu Ala Thr Val Arg Tyr Thr Ala Leu Ala
                165                 170                 175

Leu Gly Glu Asp Gly Ile Lys Val Asn Ala Val Ser Ala Gly Pro Ile
            180                 185                 190

Lys Thr Leu Ala Ala Ser Gly Ile Ser Asn Phe Lys Lys Met Leu Asp
        195                 200                 205

Tyr Asn Ala Met Val Ser Pro Leu Lys Lys Asn Val Asp Ile Met Glu
    210                 215                 220

Val Gly Asn Thr Val Ala Met Leu Cys Ser Asp Met Ala Thr Gly Ile
225                 230                 235                 240

Thr Gly Glu Val Val His Val Asp Ala Gly Tyr His Cys Val Ser Met
                245                 250                 255

Gly Asn Val Leu
            260

<210> SEQ ID NO 6
<211> LENGTH: 262
<212> TYPE: PRT
<213> ORGANISM: Haemophilus influenzae

<400> SEQUENCE: 6

Met Gly Phe Leu Thr Gly Lys Arg Ile Leu Val Thr Gly Leu Ala Ser
1               5                   10                  15

Asn Arg Ser Ile Ala Tyr Gly Ile Ala Lys Ser Met Lys Glu Gln Gly
            20                  25                  30

Ala Glu Leu Ala Phe Thr Tyr Leu Asn Asp Lys Leu Gln Pro Arg Val
        35                  40                  45

Glu Glu Phe Ala Lys Glu Phe Gly Ser Asp Ile Val Leu Pro Leu Asp
    50                  55                  60

```
Val Ala Thr Asp Glu Ser Ile Gln Asn Cys Phe Ala Glu Leu Ser Lys
 65                  70                  75                  80

Arg Trp Asp Lys Phe Asp Gly Phe Ile His Ala Ile Ala Phe Ala Pro
                 85                  90                  95

Gly Asp Gln Leu Asp Gly Asp Tyr Val Asn Ala Ala Thr Arg Glu Gly
            100                 105                 110

Tyr Arg Ile Ala His Asp Ile Ser Ala Tyr Ser Phe Val Ala Met Ala
        115                 120                 125

Gln Ala Ala Arg Pro Tyr Leu Asn Pro Asn Ala Ala Leu Leu Thr Leu
130                 135                 140

Ser Tyr Leu Gly Ala Glu Arg Ala Ile Pro Asn Tyr Asn Val Met Cys
145                 150                 155                 160

Leu Ala Lys Ala Ser Leu Glu Ala Ala Thr Arg Val Met Ala Ala Asp
                165                 170                 175

Leu Gly Lys Glu Gly Ile Arg Val Asn Ala Ile Ser Ala Gly Pro Ile
            180                 185                 190

Arg Thr Leu Ala Ala Ser Gly Ile Lys Asn Phe Lys Lys Met Leu Ser
        195                 200                 205

Thr Phe Glu Lys Thr Ala Ala Leu Arg Arg Thr Val Thr Ile Glu Asp
    210                 215                 220

Val Gly Asn Ser Ala Ala Phe Leu Cys Ser Asp Leu Ala Ser Gly Ile
225                 230                 235                 240

Thr Gly Glu Ile Val His Val Asp Ala Gly Phe Ser Ile Thr Ala Met
                245                 250                 255

Gly Glu Leu Gly Glu Glu
            260

<210> SEQ ID NO 7
<211> LENGTH: 261
<212> TYPE: PRT
<213> ORGANISM: Neisseria gonorrhoeae

<400> SEQUENCE: 7

Met Gly Phe Leu Gln Gly Lys Lys Ile Leu Ile Thr Gly Met Ile Ser
 1                5                  10                  15

Glu Arg Ser Ile Ala Tyr Gly Ile Ala Lys Ala Cys Arg Glu Gln Gly
                 20                  25                  30

Ala Glu Leu Ala Phe Thr Tyr Val Val Asp Lys Leu Glu Glu Arg Val
             35                  40                  45

Arg Lys Met Ala Ala Glu Leu Asp Ser Glu Leu Val Phe Arg Cys Asp
 50                  55                  60

Val Ala Ser Asp Asp Glu Ile Asn Gln Val Phe Ala Asp Leu Gly Lys
 65                  70                  75                  80

His Trp Asp Gly Leu Asp Gly Leu Val His Ser Ile Gly Phe Ala Pro
                 85                  90                  95

Lys Glu Ala Leu Ser Gly Asp Phe Leu Asp Ser Ile Ser Arg Glu Ala
            100                 105                 110

Phe Asn Thr Ala His Glu Ile Ser Ala Tyr Ser Leu Pro Ala Leu Ala
        115                 120                 125

Lys Ala Ala Arg Pro Met Met Arg Gly Arg Asn Ser Ala Ile Val Ala
130                 135                 140

Leu Ser Tyr Leu Gly Ala Val Arg Ala Ile Pro Asn Tyr Asn Val Met
145                 150                 155                 160

Gly Met Ala Lys Ala Ser Leu Glu Ala Gly Ile Arg Phe Thr Ala Ala
```

```
            165                 170                 175
Cys Leu Gly Lys Glu Gly Ile Arg Cys Asn Gly Ile Ser Ala Gly Pro
            180                 185                 190

Ile Lys Thr Leu Ala Ala Ser Gly Ile Ala Asp Phe Gly Lys Leu Leu
            195                 200                 205

Gly His Val Ala Ala His Asn Pro Leu Arg Arg Asn Val Thr Ile Glu
            210                 215                 220

Glu Val Gly Asn Thr Ala Ala Phe Leu Leu Ser Asp Leu Ser Ser Gly
225                 230                 235                 240

Ile Thr Gly Glu Ile Thr Tyr Val Asp Gly Gly Tyr Ser Ile Asn Ala
                245                 250                 255

Leu Ser Thr Glu Gly
            260

<210> SEQ ID NO 8
<211> LENGTH: 261
<212> TYPE: PRT
<213> ORGANISM: Neisseria meningitidis

<400> SEQUENCE: 8

Met Gly Phe Leu Gln Gly Lys Lys Ile Leu Ile Thr Gly Met Ile Ser
1               5                   10                  15

Glu Arg Ser Ile Ala Tyr Gly Ile Ala Lys Ala Cys Arg Glu Gln Gly
            20                  25                  30

Ala Glu Leu Ala Phe Thr Tyr Val Val Asp Lys Leu Glu Glu Arg Val
            35                  40                  45

Arg Lys Met Ala Ala Glu Leu Asp Ser Glu Leu Val Phe Arg Cys Asp
        50                  55                  60

Val Ala Ser Asp Asp Glu Ile Asn Gln Val Phe Ala Asp Leu Gly Lys
65                  70                  75                  80

His Trp Asp Gly Leu Asp Gly Leu Val His Ser Ile Gly Phe Ala Pro
                85                  90                  95

Lys Glu Ala Leu Ser Gly Asp Phe Leu Asp Ser Ile Ser Arg Glu Ala
            100                 105                 110

Phe Asn Thr Ala His Glu Ile Ser Ala Tyr Ser Leu Pro Ala Leu Ala
            115                 120                 125

Lys Ala Ala Arg Pro Met Met Arg Gly Arg Asn Ser Ala Ile Val Ala
            130                 135                 140

Leu Ser Tyr Leu Gly Ala Val Arg Ala Ile Pro Asn Tyr Asn Val Met
145                 150                 155                 160

Gly Met Ala Lys Ala Ser Leu Glu Ala Gly Ile Arg Phe Thr Ala Ala
                165                 170                 175

Cys Leu Gly Lys Glu Gly Ile Arg Cys Asn Gly Ile Ser Ala Gly Pro
            180                 185                 190

Ile Lys Thr Leu Ala Ala Ser Gly Ile Ala Asp Phe Gly Lys Leu Leu
            195                 200                 205

Gly His Val Ala Ala His Asn Pro Leu Arg Arg Asn Val Thr Ile Glu
            210                 215                 220

Glu Val Gly Asn Thr Ala Ala Phe Leu Leu Ser Asp Leu Ser Ser Gly
225                 230                 235                 240

Ile Thr Gly Glu Ile Thr Tyr Val Asp Gly Gly Tyr Ser Ile Asn Ala
                245                 250                 255

Leu Ser Thr Glu Gly
            260
```

<210> SEQ ID NO 9
<211> LENGTH: 274
<212> TYPE: PRT
<213> ORGANISM: Moraxella catarrhalis

<400> SEQUENCE: 9

Met Leu Leu Lys Gly Gln Arg Phe Val Val Thr Gly Ile Ala Ser Lys
1               5                   10                  15

Leu Ser Ile Ala Trp Ala Ile Ala Glu Ser Leu His Arg Glu Gly Ala
            20                  25                  30

Gln Leu Ile Leu Thr Tyr Pro Asn Asp Lys Ile Lys Lys Arg Val Asp
        35                  40                  45

Met Ala Ala Glu Ala Phe Asp Ala Val Ala Val Ile Glu Cys Asp Val
    50                  55                  60

Gly Ser Asp Glu Ser Ile Gln Val Cys Phe Asp Glu Ile Ala Lys His
65                  70                  75                  80

Trp Gly Val Gly Asp Asp Lys Gly Ile Asp Gly Ile Val His Ala Ile
                85                  90                  95

Gly Phe Ala Pro Ala Asp Gln Leu Asp Gly Asp Phe Thr Gln Ala Thr
            100                 105                 110

Thr Arg Glu Gly Ser Gln Ile Ala His Asp Ile Ser Ser Tyr Ser Phe
        115                 120                 125

Val Ala Leu Ala Lys Ala Gly Arg Glu Leu Leu Ala Ala Arg Gln Gly
    130                 135                 140

Ser Leu Leu Thr Leu Thr Tyr Glu Gly Ser Ile Ser Val Leu Pro Asn
145                 150                 155                 160

Tyr Asn Val Met Gly Met Ala Lys Ala Ser Leu Glu Ala Ser Val Arg
                165                 170                 175

Tyr Leu Ala Ser Ser Leu Gly Gly Glu Gly Ile Arg Val Asn Ala Ile
            180                 185                 190

Ser Ala Gly Pro Ile Arg Thr Leu Ala Ala Ser Gly Ile Lys Ser Phe
        195                 200                 205

Arg Arg Met Leu Asp Val Ser Glu Lys Ile Ala Pro Leu Gly Arg Asn
    210                 215                 220

Val Ser Gln Glu Glu Val Gly Asn Ala Ala Leu Phe Leu Leu Ser Pro
225                 230                 235                 240

Trp Ala Ser Gly Ile Thr Gly Glu Ile Leu Phe Val Asp Ala Gly Phe
                245                 250                 255

Asn Thr Val Ala Ile Ser Glu Lys Ile Met Met Ala Gly Asp Gly
            260                 265                 270

Glu Gln

<210> SEQ ID NO 10
<211> LENGTH: 262
<212> TYPE: PRT
<213> ORGANISM: Proteus mirabilis

<400> SEQUENCE: 10

Met Gly Phe Met Thr Gly Lys Arg Ile Leu Ile Thr Gly Val Ala Ser
1               5                   10                  15

Lys Leu Ser Ile Ala Tyr Gly Ile Ala Lys Ala Met His Asp Gln Gly
            20                  25                  30

Ala Glu Leu Ala Phe Thr Tyr Gln Asn Glu Lys Leu Lys Pro Arg Val
        35                  40                  45

Glu Glu Phe Ala Ala Ser Leu Asn Ser Asn Ile Val Leu Glu Cys Asp

-continued

```
Val Ser Lys Asp Glu Ser Ile Asp Ala Met Tyr Ala Glu Leu Ala Lys
 65                  70                  75                  80

Val Trp Pro Lys Tyr Asp Gly Phe Val His Ser Ile Gly Phe Ala Pro
                 85                  90                  95

Ala Asp Gln Leu Asp Gly Asp Tyr Val Asn Ala Val Thr Arg Glu Gly
            100                 105                 110

Phe Lys Ile Ala His Asp Ile Ser Ala Tyr Ser Phe Val Ala Met Ala
        115                 120                 125

Lys Ala Ser Arg Ala Met Leu Asn Pro Asn Ser Ala Leu Leu Thr Leu
130                 135                 140

Thr Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Ile Arg Val Asn Gly Ile Ser Ala Gly Pro Ile
            180                 185                 190

Arg Thr Leu Ala Ala Ser Gly Ile Lys Asp Phe Arg Lys Met Leu Asn
        195                 200                 205

His Cys Glu Ser Val Thr Pro Leu Arg Arg Thr Val Thr Thr Glu Asp
210                 215                 220

Val Gly Asn Thr Ala Ala Phe Leu Cys Ser Asp Leu Ser Gly Gly Ile
225                 230                 235                 240

Thr Gly Glu Ile Ile His Val Asp Gly Gly Phe Ser Ile Ala Ala Met
                245                 250                 255

Asn Glu Leu Glu Leu Lys
            260

<210> SEQ ID NO 11
<211> LENGTH: 275
<212> TYPE: PRT
<213> ORGANISM: Helicobacter pylori

<400> SEQUENCE: 11

Met Gly Phe Leu Lys Gly Lys Lys Gly Leu Ile Val Gly Val Ala Asn
 1               5                  10                  15

Asn Lys Ser Ile Ala Tyr Gly Ile Ala Gln Ser Cys Phe Asn Gln Gly
                20                  25                  30

Ala Thr Leu Ala Phe Thr Tyr Leu Asn Glu Ser Leu Glu Lys Arg Val
            35                  40                  45

Arg Pro Ile Ala Gln Glu Leu Asn Ser Pro Tyr Val Tyr Glu Leu Asp
        50                  55                  60

Val Ser Lys Glu Glu His Phe Lys Ser Leu Tyr Asn Ser Val Lys Lys
 65                  70                  75                  80

Asp Leu Gly Ser Leu Asp Phe Ile Val His Ser Val Ala Phe Ala Pro
                 85                  90                  95

Lys Glu Ala Leu Glu Gly Ser Leu Leu Glu Thr Ser Lys Ser Ala Phe
            100                 105                 110

Asn Thr Ala Met Glu Ile Ser Val Tyr Ser Leu Ile Glu Leu Thr Asn
        115                 120                 125

Thr Leu Lys Pro Leu Leu Asn Asn Gly Ala Ser Val Leu Thr Leu Ser
130                 135                 140

Tyr Leu Gly Ser Thr Lys Tyr Met Ala His Tyr Asn Val Met Gly Leu
145                 150                 155                 160
```

Ala Lys Ala Ala Leu Glu Ser Ala Val Arg Tyr Leu Ala Val Asp Leu
                165                 170                 175

Gly Lys His His Ile Arg Val Asn Ala Leu Ser Ala Gly Pro Ile Arg
            180                 185                 190

Thr Leu Ala Ser Ser Gly Ile Ala Asp Phe Arg Met Ile Leu Lys Trp
            195                 200                 205

Asn Glu Ile Asn Ala Pro Leu Arg Lys Asn Val Ser Leu Glu Glu Val
            210                 215                 220

Gly Asn Ala Gly Met Tyr Leu Leu Ser Ser Leu Ser Ser Gly Val Ser
225                 230                 235                 240

Gly Glu Val His Phe Val Asp Ala Gly Tyr His Val Met Gly Met Gly
                245                 250                 255

Ala Val Glu Glu Lys Asp Asn Lys Ala Thr Leu Leu Trp Asp Leu His
                260                 265                 270

Lys Glu Gln
        275

<210> SEQ ID NO 12
<211> LENGTH: 269
<212> TYPE: PRT
<213> ORGANISM: Mycobacterium tuberculosis

<400> SEQUENCE: 12

Met Thr Gly Leu Leu Asp Gly Lys Arg Ile Leu Val Ser Gly Ile Ile
1               5                   10                  15

Thr Asp Ser Ser Ile Ala Phe His Ile Ala Arg Val Ala Gln Glu Gln
                20                  25                  30

Gly Ala Gln Leu Val Leu Thr Gly Phe Asp Arg Leu Arg Leu Ile Gln
            35                  40                  45

Arg Ile Thr Asp Arg Leu Pro Ala Lys Ala Pro Leu Leu Glu Leu Asp
        50                  55                  60

Val Gln Asn Glu Glu His Leu Ala Ser Leu Ala Gly Arg Val Thr Glu
65                  70                  75                  80

Ala Ile Gly Ala Gly Asn Lys Leu Asp Gly Val Val His Ser Ile Gly
                85                  90                  95

Phe Met Pro Gln Thr Gly Met Gly Ile Asn Pro Phe Phe Asp Ala Pro
                100                 105                 110

Tyr Ala Asp Val Ser Lys Gly Ile His Ile Ser Ala Tyr Ser Tyr Ala
            115                 120                 125

Ser Met Ala Lys Ala Leu Leu Pro Ile Met Asn Pro Gly Gly Ser Ile
        130                 135                 140

Val Gly Met Asp Phe Asp Pro Ser Arg Ala Met Pro Ala Tyr Asn Trp
145                 150                 155                 160

Met Thr Val Ala Lys Ser Ala Leu Glu Ser Val Asn Arg Phe Val Ala
                165                 170                 175

Arg Glu Ala Gly Lys Tyr Gly Val Arg Ser Asn Leu Val Ala Ala Gly
            180                 185                 190

Pro Ile Arg Thr Leu Ala Met Ser Ala Ile Val Gly Gly Ala Leu Gly
        195                 200                 205

Glu Glu Ala Gly Ala Gln Ile Gln Leu Leu Glu Glu Gly Trp Asp Gln
    210                 215                 220

Arg Ala Pro Ile Gly Trp Asn Met Lys Asp Ala Thr Pro Val Ala Lys
225                 230                 235                 240

```
Thr Val Cys Ala Leu Leu Ser Asp Trp Leu Pro Ala Thr Thr Gly Asp
            245                 250                 255
Ile Ile Tyr Ala Asp Gly Gly Ala His Thr Gln Leu Leu
            260                 265
```